(12) United States Patent
Tashiro et al.

(10) Patent No.: US 8,163,705 B2
(45) Date of Patent: Apr. 24, 2012

(54) GLYCOLIPID AND USE THEREOF

(75) Inventors: Takuya Tashiro, Yokohama (JP); Kenji Mori, Yokohama (JP); Ken-ichi Fuhshuku, Yokohama (JP); Masaru Taniguchi, Yokohama (JP); Kenichiro Seino, Yokohama (JP)

(73) Assignee: Riken, Wako-shi (JP)

( * ) Notice: Subject to any disclaimer, the term of this patent is extended or adjusted under 35 U.S.C. 154(b) by 612 days.

(21) Appl. No.: 12/281,126

(22) PCT Filed: Feb. 28, 2007

(86) PCT No.: PCT/JP2007/053759
§ 371 (c)(1),
(2), (4) Date: Jan. 19, 2009

(87) PCT Pub. No.: WO2007/099999
PCT Pub. Date: Sep. 7, 2007

(65) Prior Publication Data
US 2009/0221516 A1      Sep. 3, 2009

(30) Foreign Application Priority Data
Feb. 28, 2006   (JP) .................................. 2006-054097

(51) Int. Cl.
*C07H 17/02*   (2006.01)
*A61K 31/7028*   (2006.01)
*A61P 31/04*   (2006.01)

(52) U.S. Cl. ............ 514/25; 514/61; 536/4.1; 536/17.9; 536/18.7

(58) Field of Classification Search ........................ None
See application file for complete search history.

(56) References Cited

U.S. PATENT DOCUMENTS
6,747,010 B2 * 6/2004 Taniguchi et al. .............. 514/25
2006/0148723 A1 7/2006 Yamamura et al.

FOREIGN PATENT DOCUMENTS
JP   2004-217601 A   8/2004
WO   WO 03/016326 A1   2/2003

OTHER PUBLICATIONS
Agmon et al., *Biochimica et Biophysica Acta*, 1170(1): 72-79 (1993).
Naoi et al., *Journal of Applied Biochemistry*, 6: 91-102 (1984).
Naoi et al., *Journal of Applied Biochemistry*, 3: 544-551 (1981).

* cited by examiner

*Primary Examiner* — Traviss C McIntosh, III
(74) *Attorney, Agent, or Firm* — Leydig, Voit & Mayer, Ltd.

(57) ABSTRACT

The present invention provide a compound represented by the following formula (1)

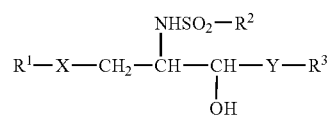

(1)

wherein each symbol is as defined in the specification, or a salt thereof.

The compound of the present invention and a salt thereof can preferentially induce production of IL-4, which is one kind of cytokines that control action of immunocytes. Therefore, it is useful for the prophylaxis or treatment of autoimmune diseases, infectious diseases and the like, and prophylaxis or treatment of diseases caused by functional promotion of Th1 cells.

12 Claims, 1 Drawing Sheet

GLYCOLIPID AND USE THEREOF

TECHNICAL FIELD

The present invention relates to a novel glycolipid and use thereof, more specifically, a novel glycolipid having a sulfonamide group and a pharmaceutical use thereof.

BACKGROUND ART

The immune system is responsible for distinguishing between self and non-self in living organisms, and protecting the self by eliminating the non-self. The immune system has an elaborate regulatory function to minimize its aggressiveness to the cells (components) of self. It is thought, however, that if the regulatory function fails, an attack on the cells (components) of itself, i.e., an autoimmune disease, develops. Autoimmune diseases are roughly divided into systemic autoimmune diseases and organ-specific autoimmune diseases. The organ-specific autoimmune diseases of these refer to diseases accompanying chronic inflammation in a particular organ or tissue (brain, liver, eyes, and articular), which is considered to be caused by immune responses to an autoantigen specific for the organ (autoimmune responses). Representative diseases include multiple sclerosis (brain, spinal cord) and rheumatoid arthritis (articular). Although different organs are affected, these diseases are thought to share the collapse of the balance of the immune system by helper T (Th) cells, resulting in a shift toward the Th1 type, as a common causal factor. Therapies for these diseases basically commonly focus on adjusting the biased immune balance of helper T cells to a shift toward the type Th2.

Natural killer (NK) T cells are immunocytes belonging to a new lymphocyte lineage that exhibit characteristics different from those of other lymphocyte lineages (T, B, and NK cells). NKT cells are related to NK cells because cytotoxic perforin granules are present therein (non-patent document 1). However, because NKT cells express not only NK cell markers, but also T cell receptors (TCRs), they have been shown to represent a new class of cells that are distinct from known cells (non-patent document 2). NKT cells are capable of producing both type Th1 cytokines (mainly interferon (IFN)-γ), which are produced by type Th1 helper T cells, and type Th2 cytokines (mainly interleukin (IL)-4), which are produced by type Th2 helper T cells (non-patent document 3); it is suggested that the balance of the immune system may be adjusted thereby (non-patent document 4). Therefore, it is possible to adjust the collapsed balance of the immune system by controlling the function of NKT cells.

The characteristic of NKT cells that is attracting the greatest attention resides in the fact that the a chain of TCR expressed in NKT cells is constant within the same species. This essentially shows that all NKT cells of the same species of organism are activated by the same substance. As such, the α chain is Vα24 for humans and Vα14 for murine animals, there is a very high homology between the two species. For the β chain, which forms a pair with the α chain, only a very limited number of kinds are known, so this TCR is called "invariable TCR".

A wide variety of sphingoglycolipids are known to exist in living organisms. Sphingoglycolipids in living organisms, generally comprising various sugars bound to ceramides via β-bonds, are present in the cell membranes of various organs, though their abundance varies among different organs (non-patent document 5). Meanwhile, it has been reported that sphingoglycolipids comprising sugars bound to ceramides via α-bonds possesses potent immunopotentiating action and antitumor activity (non-patent document 6). α-Galactosylceramides, typified by agelasphins, are glycolipids isolated from extracts from *Agelas mauritianus*, one kind of sponge, and are known to potently activate NKT cells (non-patent document 4). α-Galactosylceramides are sphingoglycolipids comprising a ceramide resulting from the acylation of the sphingosine base by a long-chain fatty acid, and galactose bound thereto in α-configuration. After being incorporated in antigen presenting cells (APCs), typified by dendritic cells (DCs) and the like, they are presented onto the cell membrane by the CD1d protein, which belongs to major histocompatibility gene complex (MHC) class I molecules. NKT cells become activated by recognizing the thus-presented complex of the CD1d protein and α-glycosylceramide by means of TCR, and various immune reactions are initiated. To date, various analogues have been synthesized, and have been investigated for the correlation between the structure and activity thereof; it has been demonstrated that α-GalCer (compound a), developed by Kirin Brewery Co., Ltd., out of the series of synthetic analogues, exhibits the highest activity, and that the corresponding β-form (β-GalCer) has no immunomodulating activity.

In recent years, with a focus on the above-described functions of NKT cells, a therapeutic drug containing α-GalCer as an active ingredient has been proposed and developed. However, administration of α-GalCer induces the production of IL-4, a cytokine that suppresses autoimmune diseases, as desired, but at the same time it induces the production of IFN-γ, a cytokine that exacerbates autoimmune diseases. As a result, the effects of both are cancelled each other, posing the problem of a lack of therapeutic effect on autoimmune diseases.

A group of Yamamura et al. recently developed OCH (compound b), a glycolipid that induces NKT cells to preferentially produce IL-4, a cytokine that suppresses autoimmune diseases (patent document 1, non-patent documents 7, 8 and 9). OCH is reported to induce the preferential production of IL-4 by shortening the alkyl side chain of α-GalCer to weaken the interaction thereof with the CD1d protein. However, this method is faulty in that the time of activation of NKT cells is short because the stability of the complex of the ligand OCH and the CD1d protein is low, and the absolute amount of IL-4 produced is small. For this reason, it is problematic that a large amount of OCH must be administered to obtain a desired effect.

Furthermore, a report is available concluding that glycolipids having an aliphatic amide group or an aliphatic sulfonamide group are useful as immunomodulator (patent document 2). However, cytokine production by such glycolipids has not been demonstrated, nor is there any suggestion of the selectivity thereof.

patent reference 1: WO 2003/016326
patent reference 2: JP-A-2001-354666
non-patent reference 1: Proc. Natl. Acad. Sci. USA 1998, 95, 5690-5693
non-patent reference 2: J. Immunol. 1995, 155, 2972-2983
non-patent reference 3: J. Immunol. 1998, 161, 3271-3281
non-patent reference 4: Science, 1997, 278, 1626-1629
non-patent reference 5: Biochim. Biophys. Acta 1973, 315-335
non-patent reference 6: J. Med. Chem. 1995, 38, 2176-2187
non-patent reference 7: J. Org. Chem. 2005, 70, 2398-2401
non-patent reference 8: Tetrahedron Lett. 2005, 46, 5043-5047
non-patent reference 9: Nature 2001, 413, 531-534

DISCLOSURE OF THE INVENTION

Problems to be Solved by the Invention

The present invention has been made in view of such actual condition, and its problem to be solved is provision of a novel compound effective for the prophylaxis or treatment and the like of autoimmune diseases and an intermediate useful for the synthesis of the compound. The present invention also aims to provide a pharmaceutical agent useful for the prophylaxis or treatment of autoimmune diseases and the like.

Means of Solving the Problems

The present inventors have conducted intensive studies in an attempt to solve the aforementioned problems and found that a compound wherein an amide bond which is a binding site characteristic of a glycolipid such as glycosylceramide and the like is converted to a sulfonamide bond has a selective immune regulatory capability and is extremely effective for the prophylaxis or treatment of autoimmune diseases, infectious diseases and the like, which resulted in the completion of the present invention.

Accordingly, the present invention provides the following.

[1] A compound represented by the following formula (1):

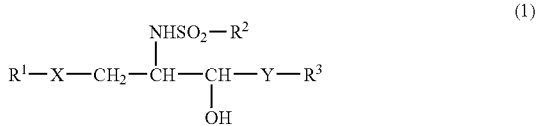

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —$CH_2$— or —NH—, Y is —$CH_2$—, —CH(OH)— or —CH=CH—, or a salt thereof.

[2] The compound of the above-mentioned [1], wherein $R^1$ is α-D-galactopyranosyl, or a salt thereof.

[3] The compound of the above-mentioned [1] or [2], wherein $R^2$ is an aromatic hydrocarbon group optionally having substituent(s) or a salt thereof.

[4] The compound of any of the above-mentioned [1] to [3], wherein $R^3$ is a $C_{1-21}$ alkyl group optionally having substituent(s), or a salt thereof.

[5] The compound of any of the above-mentioned [1] to [4], wherein X is an oxygen atom, or a salt thereof.

[6] The compound of any of the above-mentioned [1] to [5], wherein Y is —CH(OH)—, or a salt thereof.

[7] A compound represented by the following formula (2):

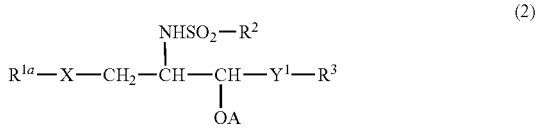

wherein $R^{1a}$ is an aldopyranose residue wherein the hydroxyl group is protected, $Y^1$ is —$CH_2$—, —CH(OA)- or —CH=CH—, A is a hydrogen atom or a hydroxyl-protecting group, and $R^2$, $R^3$ and X are as defined above, or a salt thereof.

[8] A pharmaceutical agent comprising the compound represented by the above-mentioned formula (1), or a salt thereof.

[9] An agent for the prophylaxis or treatment of an autoimmune disease or an infectious disease, comprising a compound represented by the above-mentioned formula (1), or a salt thereof.

[10] An NKT cell activator comprising a compound represented by the above-mentioned formula (1), or a salt thereof.

[11] A selective IL-4 production inducer comprising a compound represented by the above-mentioned formula (1), or a salt thereof.

[12] An agent for the prophylaxis or treatment of a disease caused by functional promotion of Th1 cells, comprising a compound represented by the above-mentioned formula (1), or a salt thereof.

[13] An agent for the prophylaxis or treatment of an autoimmune disease or an infectious disease, comprising a compound represented by the following formula (3):

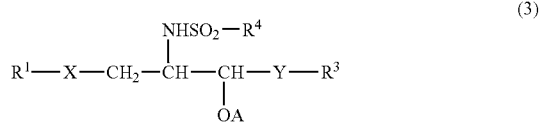

wherein $R^4$ is a $C_{1-28}$ aliphatic hydrocarbon group optionally having substituent(s), and $R^1$, $R^3$, X and Y are as defined above, or a salt thereof.

[14] A selective IL-4 production inducer, comprising a compound represented by the above-mentioned formula (3) or a salt thereof.

[15] An agent for the prophylaxis or treatment of a disease caused by functional promotion of Th1 cells, comprising a compound represented by the above-mentioned formula (3), or a salt thereof.

Effect of the Invention

According to the present invention, a novel glycolipid having a sulfonamide group, which is effective for the prophylaxis or treatment of autoimmune diseases and the like, and an intermediate useful for the synthesis of the glycolipid are provided.

Because glycolipids relating to the present invention have a much higher polarity than that of conventionally known ceramides, thanks to the introduction of a sulfonamide group, it is possible to easily form a complex with the CD1d protein of APC, and it is also possible to improve the stability of the complex. Therefore, when administered, a pharmaceutical containing a glycolipid relating to the present invention as an active ingredient easily forms a complex with the CD1d protein and is presented to NKT cells; the NKT cells that have recognized this complex can induce the preferential production of IL-4, a kind of type Th2 cytokine, out of their own immune adjust functions. This enables, without adverse reactions of special note, prophylaxis or treatment of autoimmune diseases and prophylaxis or treatment of diseases resulting from functional accentuation of Th1 cells. Because IL-4 is also involved in the increase in cytotoxicity, it is also effective in the prophylaxis or treatment of infectious diseases.

Because glycolipids relating to the present invention significantly contribute to the stabilization of the complex with the CD1d protein, even a small dose of administration enables potent activation of NKT cells to increase the amount of IL-4 produced compared to conventionally known ceramides.

Furthermore, glycolipids having a sulfonamide group, relating to the present invention, can also be used as reagents for biological tests or studies.

BEST MODE FOR CARRYING OUT THE INVENTION

Figure 1:
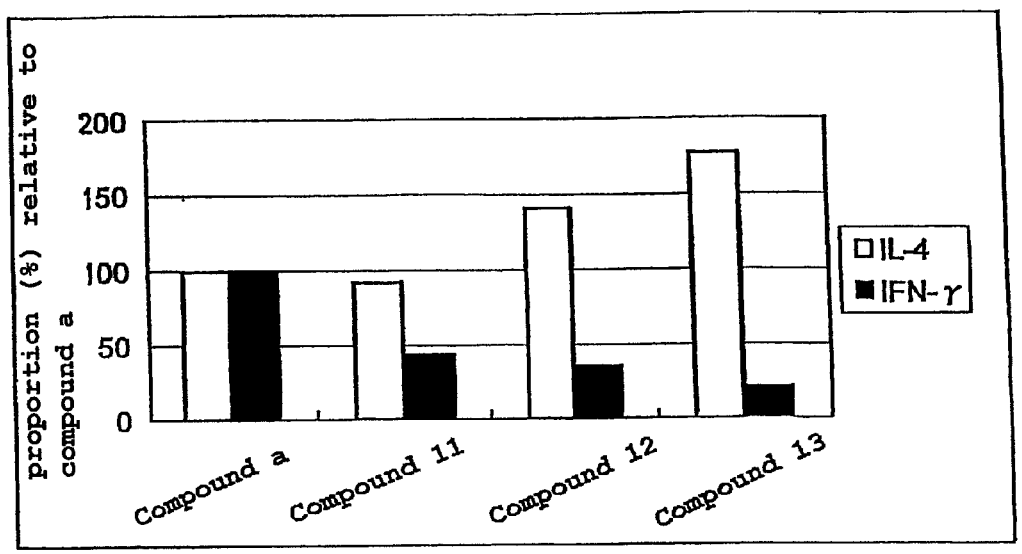
FIG. 1 shows the measurement results of IFN-γ production amount and IL-4 production amount in Experimental Example 1.

The present invention is explained in detail in the following by referring to preferable embodiments.

First, the definitions of the symbols to be used in each formula of the present invention are explained.

$R^1$ is an aldopyranose residue, and $R^{1a}$ is an aldopyranose residue wherein the hydroxyl group is protected, wherein the aldopyranose residue means a residue excluding the reduced terminal hydroxyl group of aldopyranose. Examples of the aldopyranose residue include α-D-galactopyranosyl, α-D-glucopyranosyl, β-D-galactopyranosyl, β-D-glucopyranosyl and the like. Particularly, α-D-galactopyranosyl is preferable from the aspect of pharmacological effect.

Examples of the hydroxyl-protecting group of sugar of the aldopyranose residue include acyl group, t-butyldimethylsilyl (TBS) group, trimethylsilyl (TMS) group, benzyl (Bn) group, p-methoxybenzyl (PMB) group and the like.

In the present specification, the acyl group means a formyl group; a $C_{1-12}$ linear or branched, or $C_{3-10}$ cyclic, alkyl-carbonyl group (e.g., acetyl group, propionyl group, butyryl group, isobutyryl group, valeryl group, pivaloyl group, hexanoyl group, acryloyl group, methacryloyl group); or a $C_{6-14}$ aryl-carbonyl group (e.g., benzoyl group, naphthoyl group). The aryl group of the aryl-carbonyl group is a monocyclic-tricyclic aromatic hydrocarbon group, such as a phenyl group, a naphthyl group, an anthryl group and a phenanthryl group. Of these, as the acyl group, a formyl group, an acetyl group, a propionyl group, a butyryl group, an isobutyryl group, a benzoyl group, a naphthoyl group and the like are preferable, and an acetyl group and a benzoyl group are more preferable.

As the hydroxyl-protecting group of the sugar of the aldopyranose residue, a benzyl (Bn) group and a p-methoxybenzyl (PMB) group are preferable.

$R^2$ is an aromatic group optionally having substituent(s). The aromatic group in the present specification is a concept encompassing not only an aromatic hydrocarbon group but also an aromatic heterocyclic group, which may be monocyclic or polycyclic as long as it has aromaticity. Examples of the aromatic hydrocarbon group include a $C_{6-14}$ aryl group derived from benzene, naphthalene, anthracene and the like. Examples of the aromatic heterocyclic group include preferably 5- or 6-membered monocyclic aromatic heterocyclic group, a group derived from a fused ring of 5- or 6-membered monocyclic aromatic heterocycles, and a group derived from a fused ring of a 5- or 6-membered monocyclic aromatic heterocycle and a benzene ring. Specific examples thereof include groups derived from furan, pyrrole, thiophene, pyridine, pyrazine, pyrimidine, triazine, tetrazine, oxazole, isoxazole, imidazole, benzimidazole, pyrazole, triazole, thiazole, indole, quinoline, isoquinoline, benzothiazole, benzoxathiin, phenanthridine, phenanthrene, quinoxaline, phenazine, polyazaphenanthrene, oxadiazine, benzooxadiazine, dioxadiazine, carbazole, acridine, pyrrocholine and the like. Of these, an aromatic hydrocarbon group is preferable, and a phenyl group and a naphthyl group are more preferable.

Examples of the substituent of the aromatic group include electron-releasing groups, for example, halogens (preferably chlorine atom, fluorine atom); alkyl groups (preferably $C_{1-24}$, more preferably $C_{1-16}$, more preferably $C_{1-10}$, particularly preferably $C_{1-4}$) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a cyclopentyl group, a cyclohexyl group and the like; alkenyl groups (preferably $C_{2-24}$, more preferably $C_{2-16}$, more preferably $C_{2-10}$, particularly preferably $C_{2-4}$) such as a vinyl group, a propenyl group, a butenyl group and the like; alkynyl groups (preferably $C_{2-24}$, more preferably $C_{2-16}$, more preferably $C_{2-10}$, particularly preferably $C_{2-4}$) such as an ethynyl group, a propargyl group, a butynyl group, a pentynyl group and the like; a phenyl group; alkoxy groups (preferably $C_{1-24}$, more preferably $C_{1-16}$, more preferably $C_{1-10}$, particularly preferably $C_{1-4}$) such as a methoxy group, an ethoxy group, a propoxy group, an isopropoxy group, a butoxy group, a tert-butoxy group and the like; aryloxy groups (preferably $C_{6-14}$) such as a phenoxy group and the like; a hydroxyl group; an amino group; alkyl (as defined for the alkyl group) amino groups such as a methylamino group, a dimethylamino group, an ethylamino group, a diethylamino group and the like; and the like, and electron-withdrawing groups, for example, a carboxyl group; an alkoxy (as defined for the alkoxy group) carbonyl group; an acyl group (preferably $C_{1-24}$ linear or branched alkyl-carbonyl group); a carbamoyl group; a trifluoromethyl group; alkyl (as defined for the alkyl group) carbonylamino groups such as an acetamido group and the like, aryl (preferably $C_{6-14}$) carbonylamino groups such as a benzoylamino group and the like; and the like. The above-mentioned alkyl group, the alkyl moiety of the alkoxy group, the phenyl group and the like may be substituted by at least one kind from the aforementioned halogen, alkyl group, alkenyl group, alkynyl group, phenyl group, alkoxy group, hydroxyl group, amino group and alkylamino group, or these substituents may be bonded to form a ring.

Particularly, as the substituent of the aromatic group, an alkyl group is preferable, a $C_{1-4}$ alkyl group is more preferable, and a methyl group is further preferable. Therefore, as the substituted aromatic group, an alkyl-substituted phenyl group is preferable, and one wherein at least one of the ortho-position, meta-position and para-position of the phenyl group is substituted by a $C_{1-4}$ alkyl group, more preferably a methyl group, is preferable.

$R^3$ is a $C_{1-21}$ hydrocarbon group optionally having substituent(s). In the present specification, the hydrocarbon group is a concept encompassing a substituted or unsubstituted $C_{1-21}$ alkyl group, a $C_{2-21}$ alkenyl group, a $C_{2-21}$ alkynyl group, a $C_{3-14}$ cycloalkyl group, a $C_{3-14}$ cycloalkenyl group and a $C_{6-4}$ aryl group, which may be linear, branched or cyclic, or may be a saturated hydrocarbon group or an unsaturated hydrocarbon group, and optionally having an unsaturated bond in a molecule or at the terminal. As such hydrocarbon group, a substitution or unsubstituted $C_{1-21}$ alkyl group is preferable. In addition, examples of the substituent of such hydrocarbon group include groups similar to the substituents of the aforementioned aromatic group, where at least one kind of such substituents can be possessed. Of those, a linear alkyl group is preferable. While the carbon number of $R^3$ is 1-21, it is preferably 1-15, more preferably 10-15. When the carbon number exceeds 21, the effect of the invention is difficult to obtain.

$R^4$ is a $C_{1-28}$ aliphatic hydrocarbon group optionally having substituent(s). Examples of the aliphatic hydrocarbon group include substituted or unsubstituted $C_{1-28}$ alkyl group, a $C_{2-28}$ alkenyl group, a $C_{2-28}$ alkynyl group, a $C_{3-28}$ cycloalkyl group and a $C_{3-28}$ cycloalkenyl group, with preference given to substituted or unsubstituted $C_{1-28}$ alkyl group. While the carbon number of $R^4$ is 1-28, it is preferably 16-28, more preferably 16-25. When the carbon number exceeds 28, the selectivity of the activity becomes lower.

X is an oxygen atom, a sulfur atom, —$CH_2$— or —NH—, with preference given to an oxygen atom.

Y is —$CH_2$—, —CH(OH)— or —CH=CH—, with preference given to —CH(OH)—.

$Y^1$ is —$CH_2$—, —CH(OA)- or —CH=CH—, with preference given to —CH(OA)-.

A is a hydrogen atom or a hydroxyl-protecting group, and as the hydroxyl-protecting group, an acyl group (as defined above), a t-butyldimethylsilyl (TBS) group, a benzyl (Bn) group, a p-methoxybenzyl (PMB) group, an acetonide group and the like can be mentioned. Of these, when X is an oxygen atom, a sulfur atom or —NH—, a TBS group is preferable, and when X is —$CH_2$—, an acetonide group is preferable.

A compound represented by the general formula (1) above (hereinafter referred to as "compound (1)"; the same applies to the designation of compounds represented by respective formulas) involves α-form and β-form structural isomers resulting from the aldopyranose residue, and may be in the α-form, β-form or a mixture thereof, with preference given to the α-form from the viewpoint of pharmacological effect.

Compound (1) has at least four kinds of optical isomers resulting from the asymmetric carbon in the lipid moiety thereof; in the present invention, compound (1) may be a single optically active substance, or a mixture of two or more kinds of optically active substances in an optionally chosen ratio (including racemates). The asymmetric carbon to which —$NHSO_2R^2$ binds is preferably in the S-configuration, and the asymmetric carbon to which OH binds is preferably in the configuration in the anti-relation to the asymmetric carbon to which —$NHSO_2R^2$ binds. When Y is —CH(OH)—, the asymmetric carbon in —CH(OH)— is preferably in the R-configuration; this also applies to $Y^1$.

For compounds (2) and (3), those shown above can be mentioned as suitable.

Salts of compound (1) are preferably pharmacologically acceptable salts; examples include inorganic acid salts such as hydrochlorides, hydrobromides, hydroiodides, sulfates, nitrates, and phosphates; organic acid salts such as succinates, fumarates, acetates, methanesulfonates, and toluenesulfonates; alkali metal salts such as sodium salts and potassium salts; alkaline earth metal salts such as magnesium salts and calcium salts; ammonium salts such as ammonium salts and alkylammonium salts; and the like. The same applies to compounds (2) and (3).

Specific examples of preferable compound (1) of the present invention are shown in Tables 1-3, which are not to be construed as limitative.

TABLE 1

| compound No. | $R^1$ | $R^2$ | $R^3$ | X | Y |
|---|---|---|---|---|---|
| 11 | (aldopyranose with OH groups) | 4-methylphenyl | —$(CH_2)_{13}CH_3$ | O | —CH(OH)— |
| 12 | (aldopyranose with OH groups) | 2-methylphenyl | —$(CH_2)_{13}CH_3$ | O | —CH(OH)— |
| 13 | (aldopyranose with OH groups) | 3-methylphenyl | —$(CH_2)_{13}CH_3$ | O | —CH(OH)— |
| 14 | (aldopyranose with OH groups) | 4-tert-Bu-phenyl | —$(CH_2)_{13}CH_3$ | O | —CH(OH)— |

TABLE 1-continued
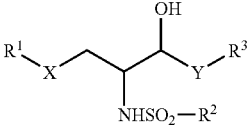
| compound No. | R¹ | R² | R³ | X | Y |
|---|---|---|---|---|---|
| 15 | 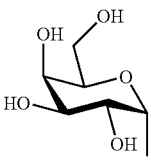 | 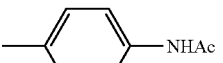 | —(CH$_2$)$_{13}$CH$_3$ | O | —CH—<br>\|<br>OH |
| 16 | 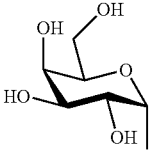 | 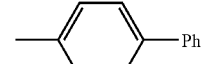 | —(CH$_2$)$_{13}$CH$_3$ | O | —CH—<br>\|<br>OH |
| 17 | 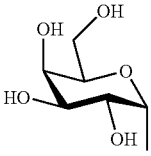 | 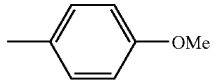 | —(CH$_2$)$_{13}$CH$_3$ | O | —CH—<br>\|<br>OH |
| 18 | 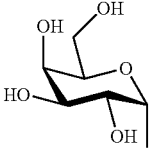 | 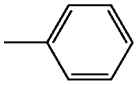 | —(CH$_2$)$_{13}$CH$_3$ | O | —CH—<br>\|<br>OH |
| 19 | 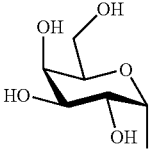 | 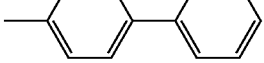 | —(CH$_2$)$_{13}$CH$_3$ | O | —CH—<br>\|<br>OH |
| 20 | 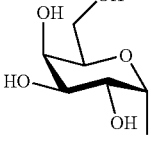 | 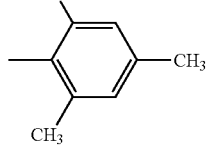 | —(CH$_2$)$_{13}$CH$_3$ | O | —CH—<br>\|<br>OH |
| 21 | 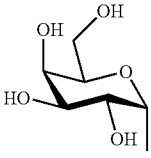 | 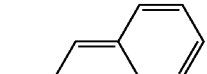 | —(CH$_2$)$_{13}$CH$_3$ | O | —CH—<br>\|<br>OH |

TABLE 2

Structure: R¹–X–CH₂–C(NHSO₂–R²)–CH(OH)–Y–R³

| compound No. | R¹ | R² | R³ | X | Y |
|---|---|---|---|---|---|
| 22 | β-D-galactopyranosyl (OH, OH, HO, OH) | 4-(CF₃)-phenyl | —(CH₂)₁₃CH₃ | O | —CH(OH)— |
| 23 | β-D-galactopyranosyl | 4-F-phenyl | —(CH₂)₁₃CH₃ | O | —CH(OH)— |
| 24 | β-D-galactopyranosyl | 2,4-diF-phenyl | —(CH₂)₁₃CH₃ | O | —CH(OH)— |
| 25 | β-D-galactopyranosyl | pentafluorophenyl | —(CH₂)₁₃CH₃ | O | —CH(OH)— |
| 26 | β-D-galactopyranosyl | 4-Cl-phenyl | —(CH₂)₁₃CH₃ | O | —CH(OH)— |
| 27 | β-D-galactopyranosyl | 2,5-diCl-phenyl | —(CH₂)₁₃CH₃ | O | —CH(OH)— |
| 28 | β-D-galactopyranosyl | 2,4,6-triCl-phenyl | —(CH₂)₁₃CH₃ | O | —CH(OH)— |
| 29 | β-D-galactopyranosyl | 4-(CH₂CH₃)-phenyl | —(CH₂)₁₃CH₃ | O | —CH(OH)— |

TABLE 2-continued

[Structure: R¹–X–CH₂–C(NHSO₂–R²)–CH(OH)–Y–R³]

| compound No. | R¹ | R² | R³ | X | Y |
|---|---|---|---|---|---|
| 30 | (galactopyranose with OH, OH, HO, OH) | 4-vinylphenyl (–C₆H₄–CH=CH₂) | —(CH₂)₁₃CH₃ | O | —CH(OH)— |
| 31 | (galactopyranose with OH, OH, HO, OH) | 2,4-dimethylphenyl | —(CH₂)₁₃CH₃ | O | —CH(OH)— |

TABLE 3

[Structure: R¹–X–CH₂–C(NHSO₂–R²)–CH(OH)–Y–R³]

| compound No. | R¹ | R² | R³ | X | Y |
|---|---|---|---|---|---|
| 32 | (sugar with OH, OH, HO, OH) | 4-methylphenyl | —(CH₂)₁₃CH₃ | S | —CH(OH)— |
| 33 | (sugar with OH, OH, HO, OH) | 4-methylphenyl | —(CH₂)₁₃CH₃ | NH | —CH(OH)— |
| 34 | (sugar with OH, OH, HO, OH) | 4-methylphenyl | —(CH₂)₁₃CH₃ | CH₂ | —CH(OH)— |
| 35 | (sugar with OH, HO, HO, OH) | 4-methylphenyl | —(CH₂)₁₃CH₃ | O | —CH(OH)— |

TABLE 3-continued

| compound No. | R¹ | R² | R³ | X | Y |
|---|---|---|---|---|---|
| 36 | galactopyranose | p-tolyl | —(CH$_2$)$_{12}$CH$_3$ | O | —CH=CH— |
| 37 | galactopyranose | p-tolyl | —(CH$_2$)$_{12}$CH$_3$ | O | —CH=CH— |
| 38 | galactopyranose | p-tolyl | —(CH$_2$)$_{13}$CH$_3$ | O | —CH$_2$— |
| 39 | galactopyranose | p-tolyl | —(CH$_2$)$_{13}$CH$_3$ | O | —CH$_2$— |
| 40 | galactopyranose | p-tolyl | —(CH$_2$)$_4$CH$_3$ | O | —CH(OH)— |
| 41 | galactopyranose | p-tolyl | —(CH$_2$)$_3$CH$_3$ | O | —CH=CH— |
| 42 | galactopyranose | p-tolyl | —(CH$_2$)$_4$CH$_3$ | O | —CH$_2$— |

Among those, particularly preferable compounds are the following compounds.

[1]  (2S,3S,4R)-1-(α-D-galactopyranosyloxy)-2-(p-toluenesulfonylamino)-3,4-octadecanediol (compound 11)

[2]  (2S,3S,4R)-1-(α-D-galactopyranosyloxy)-2-(o-methylphenylsulfonylamino)-3,4-octadecanediol (compound 12)

[3]  (2S,3S,4R)-1-(α-D-galactopyranosyloxy)-2-(m-methylphenylsulfonylamino)-3,4-octadecanediol (compound 13)

Specific examples of preferable compound (3) are shown in Table 4, which are not to be construed as limitative.

TABLE 4

[Structure: R¹–X–CH₂–CH(NHSO₂–R⁴)–CH(OH)–Y–R³]

| compound No. | R¹ | R⁴ | R³ | X | Y |
|---|---|---|---|---|---|
| 43 | galactopyranosyl (OH, OH, HO, OH) | —CH₃ | —(CH₂)₁₃CH₃ | O | —CH(OH)— |
| 44 | galactopyranosyl | —CF₃ | —(CH₂)₁₃CH₃ | O | —CH(OH)— |
| 45 | galactopyranosyl | -n-Pr | —(CH₂)₁₃CH₃ | O | —CH(OH)— |
| 46 | galactopyranosyl | —CH(CH₃)₂ | —(CH₂)₁₃CH₃ | O | —CH(OH)— |
| 47 | galactopyranosyl | —(CH₂)₇CH₃ | —(CH₂)₁₃CH₃ | O | —CH(OH)— |
| 48 | galactopyranosyl | —(CH₂)₁₅CH₃ | —(CH₂)₁₃CH₃ | O | —CH(OH)— |
| 49 | galactopyranosyl | —(CH₂)₂₄CH₃ | —(CH₂)₁₃CH₃ | O | —CH(OH)— |
| 50 | galactopyranosyl | —(CH₂)₁₅CH₃ | —(CH₂)₁₂CH₃ | O | —CH=CH— |

TABLE 4-continued

![structure: R¹-X-CH₂-CH(NHSO₂-R⁴)-CH(OH)-Y-R³]

| compound No. | R¹ | R⁴ | R³ | X | Y |
|---|---|---|---|---|---|
| 51 | (glucopyranose with CH₂OH, OH, OH, HO) | —(CH₂)₁₅CH₃ | —(CH₂)₁₂CH₃ | O | —CH=CH— |
| 52 | (galactopyranose with OH, CH₂OH, HO, OH) | —(CH₂)₁₅CH₃ | —(CH₂)₁₃CH₃ | O | —CH₂— |
| 53 | (mannopyranose with CH₂OH, HO, HO, OH) | —(CH₂)₁₅CH₃ | —(CH₂)₁₃CH₃ | O | —CH₂— |

Preferable embodiment of the production method of the compound of the present invention is now explained. The compound of the present invention can be produced by various methods. Compound (1) wherein X is an oxygen atom, a sulfur atom or —NH— can be produced, for example, according to the method described in the following Scheme 1.

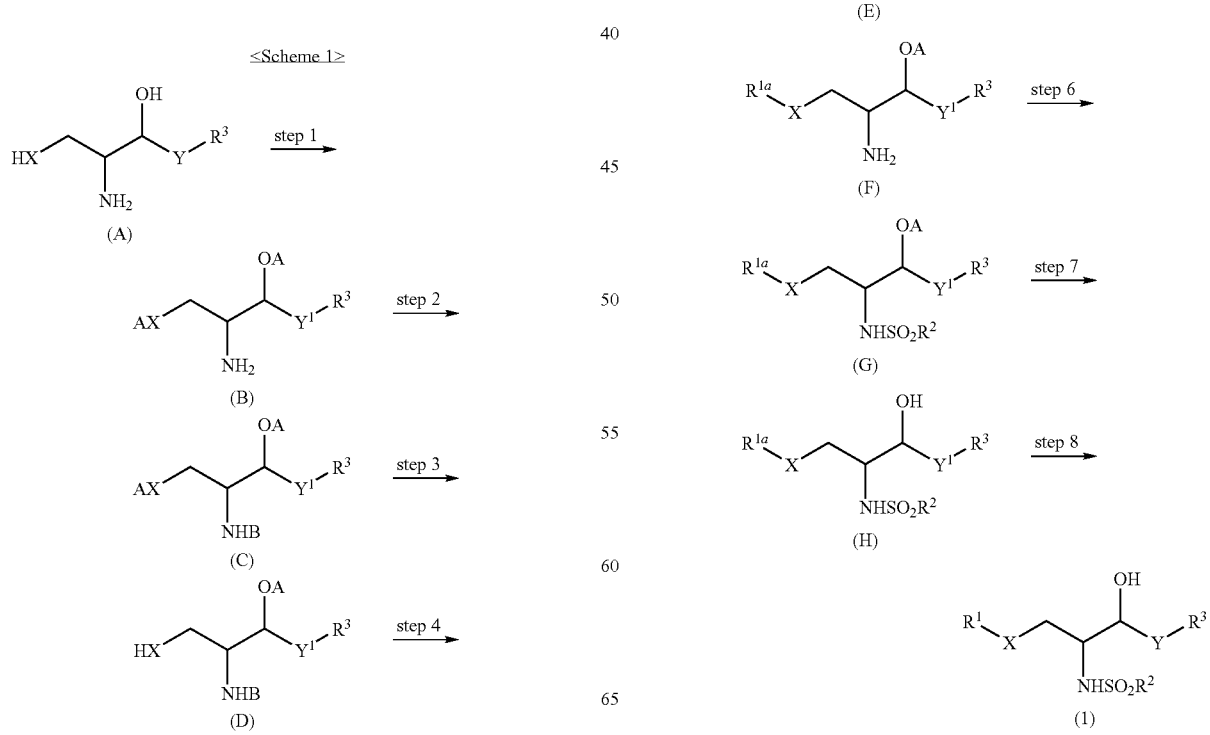

(Step 1)

Step 1 is a step for protecting the —XH and hydroxyl group of amino alcohol (A) to yield compound (B). Specifically, amino alcohol (A) is reacted with a protecting reagent in the presence of a base in an organic solvent. Bases include amino compounds such as pyridine, 2,6-lutidine, and triethylamine. When X is an oxygen atom, an organic silicon reagent is suitably used as the protecting reagent; for example, tert-butyldimethylsilyl trifluoromethanesulfonate, tert-butyldimethylsilyl chloride and the like can be used. When X is a sulfur atom, benzyl-system thioether is suitably used as the protecting reagent; examples include benzyl thioether, 4-methoxybenzyl thioether and the like. When X is —NH—, carbamate is suitably used as the protecting reagent; examples include tert-butyl carbamate, benzyl carbamate and the like. Any solvent that does not interfere with this reaction can be used; for example, halogen solvents (e.g., dichloromethane, chloroform) are suitable. The amount of base used is normally 1 to 50 fold by volume, preferably 10 to 20 fold by volume, relative to amino alcohol (A). The amount of protecting reagent used is normally 1 to 5 equivalents, preferably 1 to 2 equivalents, per hydroxyl group of amino alcohol (A). Reaction temperature is normally −20° C. to room temperature, preferably 0 to 4° C.; reaction time is normally 1 to 48 hours, preferably 12 to 24 hours. After completion of the reaction, the reaction liquid is concentrated under reduced pressure, and the residue is purified by column chromatography, whereby compound (B) can be obtained at high percent yields.

(Step 2)

Step 2 is a step for protecting the amino group of compound (B) to yield compound (C). Specifically, compound (B) is reacted with an amino group protecting reagent in an organic solvent. Examples of protecting reagents include 9-fluorenylmethyl succinimidyl carbonate, di-tert-butyl dicarbonate, and benzyl chloroformate. The amount of protecting reagent used is normally 1 to 5 equivalents, preferably 1 to 2 equivalents, relative to compound (B). As the solvent, for example, aprotic solvents are suitable, which may be used in a mixture of two or more kinds. The amount of solvent used is normally 10 to 50 fold by volume, preferably 20 to 30 fold by volume, relative to compound (B). Reaction temperature is normally 0° C. to room temperature, preferably room temperature; reaction time is normally 1 to 50 hours, preferably 12 to 24 hours. After completion of the reaction, the reaction liquid is diluted with water, and extracted with a solvent such as ether. The organic layer obtained is washed with water, saturated sodium hydrogen carbonate and the like, and dried with anhydrous magnesium sulfate and the like, after which it is filtered. The filtrate is concentrated under reduced pressure, and the residue is purified by column chromatography, whereby compound (C) can be obtained at high percent yields.

(Step 3)

Step 3 is a step for removing the protecting group A in —XA in compound (C) to yield compound (D). A method of removal is chosen according to the protecting group; for example, compound (C) and an acid are reacted in a solvent. As the acid, strong acids such as trifluoroacetic acid, p-toluenesulfonic acid, and hydrochloric acid are suitably used. The amount of acid used is normally a catalytic amount to 10 fold by volume, preferably 1 to 2 fold by volume, relative to compound (C). Reaction temperature is normally −20° C. to room temperature, preferably −10 to 0° C.; reaction time is normally 2 to 12 hours, preferably 2 to 4 hours. The solvent is preferably a water-soluble solvent, and tetrahydrofuran is particularly preferable. The amount of solvent used is normally 5 to 100 fold by volume, preferably 10 to 50 fold by volume, relative to compound (C). After completion of the reaction, compound (D) can be isolated and purified by a conventional method. For example, the reaction liquid is neutralized with a basic aqueous solution such as an aqueous solution of sodium hydroxide, and extracted with an ether solvent such as diethyl ether. The organic layer obtained is washed with a saturated aqueous solution of sodium hydrogen carbonate, saturated saline and the like, and dried with anhydrous potassium carbonate and the like. After the solution is filtered, the filtrate is concentrated under reduced pressure, and the residue may be purified by column chromatography.

(Step 4)

Step 4 is a step for aldopyranosylating compound (D) to yield compound (E). The aldopyranosylation is achieved by, for example, reacting compound (D) with an aldopyranosyl halide whose hydroxyl group is protected ($R^{1a}$—$X^1$, $X^1$ is a halogen) in a solvent in the presence of an activator. Examples of the activator include a combination of tin chloride and silver perchlorate, silver trifluoromethanesulfonate and the like. Furthermore, this reaction is desirably carried out in the presence of a dehydrant such as molecular sieves. The amount of activator used is normally 2 to 4 equivalents, preferably 3 to 4 equivalents, relative to compound (D). The amount of dehydrant used is normally 2 to 10 fold by weight, preferably 3 to 5 fold by weight, relative to compound (D). The aldopyranosyl halide whose hydroxyl group is protected is preferably one wherein the hydroxyl groups at the 2,3,4,6-positions are protected by a benzyl (Bn) group; the halogen is preferably a fluorine atom. The amount used of aldopyranosyl halide whose hydroxyl group is protected is normally 2 to 4 equivalents, preferably 2 to 3 equivalents, relative to compound (D). Reaction temperature is normally −20° C. to room temperature; reaction time is normally 2 to 12 hours, preferably 2 to 4 hours. The solvent is preferably an aprotic solvent, and tetrahydrofuran is particularly preferable. The amount of solvent used is normally 10 to 100 fold by volume, preferably 20 to 50 fold by volume, relative to compound (D). After completion of the reaction, the reaction liquid is filtered, and the filtrate is washed with saturated saline and the like and dried with anhydrous magnesium sulfate and the like. After the solution is filtered, the filtrate is concentrated under reduced pressure, and the residue is purified by column chromatography, whereby compound (E) can be obtained.

(Step 5)

Step 5 is a step for removing the protecting group B for the amino group of compound (E) to yield compound (F). A method of removal is chosen according to the protecting group; for example, compound (E) is reacted in a solvent in the presence of a base. Examples of the solvent include aprotic solvents, with preference given to DMF. As the base, morpholine, piperidine and the like are suitably used. The amount of solvent used is normally 10 to 200 fold by volume, preferably 50 to 100 fold by volume, relative to compound (E). The amount of base used is normally 10 to 200 equivalents, preferably 100 to 200 equivalents, relative to compound (E). Reaction temperature is normally −20° C. to room temperature, preferably room temperature. Reaction time is normally 0.5 to 12 hours, preferably 5 to 10 hours. After completion of the reaction, the solvent of the reaction liquid is replaced as required, and the reaction liquid is washed with water, saturated saline and the like, and dried with anhydrous potassium carbonate and the like. After the solution is filtered, the filtrate is concentrated under reduced pressure, and the residue is purified by column chromatography, whereby compound (F) can be obtained at high percent yields.

(Step 6)

Step 6 is a step for sulfonamidating compound (F) to yield compound (G). Specifically, compound (F) is reacted with an aromatic sulfonyl halide ($R^2$—$SO_2$—$X^1$, wherein $X^1$ is as defined above) in a solvent in the presence of a base. Any solvent that does not interfere with this reaction can be used; for example, halogen solvents (e.g., dichloromethane, chloroform) are suitably used. As the base, pyridine, triethylamine and the like can be mentioned, with preference given to pyridine. The amount of solvent used is normally 5 to 100 fold by volume, preferably 20 to 50 fold by volume, relative to compound (F). The amount of base used is normally 10 to 50 fold by volume, preferably 10 to 20 fold by volume, relative to compound (F). The amount of aromatic sulfonyl halide used is normally 1 to 20 equivalents, preferably 1 to 10 equivalents, relative to compound (F). Reaction temperature is normally −20° C. to room temperature, preferably 0 to 4° C.; reaction time is normally 1 to 24 hours, preferably 6 to 12 hours. After completion of the reaction, the reaction liquid is diluted with water, and extracted with an ether solvent such as diethyl ether. The organic layer obtained is washed with a saturated aqueous solution of copper sulfate, water, saturated saline and the like, and dried with anhydrous magnesium sulfate and the like. After the solution is filtered, the filtrate is concentrated under reduced pressure, and the residue is purified by column chromatography, whereby compound (G) can be obtained.

(Step 7)

Step 7 is a step for removing the protecting group A for the hydroxyl group of the lipid moiety of compound (G) to yield compound (H). Specifically, this step can be performed in the same manner as the step 3 described above.

(Step 8)

Step 8 is a step for removing the protecting group for the hydroxyl group of the aldopyranose in compound (H) to yield compound (1). Specifically, compound (H) is reacted in a solvent in the presence of hydrogen and a reducing catalyst. The solvent is suitably a mixed solvent of an alcohol solvent and a halogen solvent, preferably a mixed solvent of ethanol and chloroform. The amount of solvent used is normally 10 to 50 fold by volume, preferably 10 to 20 fold by volume, relative to compound (H). Useful reducing catalysts include palladium hydroxide, platinum oxide, Raney nickel and the like. The amount of reducing catalyst used is normally sufficiently a catalytic amount relative to compound (H). Reaction time is normally 1 to 24 hours, preferably 12 to 24 hours. Reaction temperature is normally 0° C. to room temperature, preferably room temperature. After completion of the reaction, the reaction liquid is filtered, the filtrate is concentrated under reduced pressure, and the residue is purified by column chromatography, whereby desired compound (1) can be obtained at high percent yields.

When the obtained compound (1) contains isomers, the isomers (α-form and β-form) may be separated and purified using solvents with different polarities in column chromatography. The α-form of the compound (1) may be prepared by separating and purifying the isomers through the steps 4 to 8, and using, for example, the isolated α-form as the starting compound for the next step.

Compound (3), wherein X is an oxygen atom, a sulfur atom or —NH—, can be produced using an aliphatic sulfonyl halide in place of the above-described aromatic sulfonyl halide, according to the above-described Scheme 1.

Compound (1), wherein X is —$CH_2$—, can be prepared by, for example, preparing compound (F) as described in Tetrahedron Lett. 2005, 46, 5043-5047, then preparing compound (G) in the same manner as the step 6 above, then removing the protecting group A for the hydroxyl group of the lipid moiety of compound (G) using a strong acid such as trifluoroacetic acid, p-toluenesulfonic acid, or hydrochloric acid to yield compound (H), and treating the compound (H) in the same manner as the above-described step 8. Compound (3), wherein X is —$CH_2$—, can also be produced as described above.

The agent for the prophylaxis or treatment for autoimmune diseases or infectious diseases and the like, NKT cell activator, selective IL-4 production inducer and agent for the prophylaxis or treatment for diseases resulting from functional accentuation of Th1 cells, of the present invention will now be described.

By administering compound (1), compound (3) or a salt thereof according to the present invention (hereinafter referred to as "compound (1) and the like"), it is possible to activate NKT cells to preferentially induce production of IL-4, and to prevent or treat autoimmune diseases or infectious diseases and the like without aggravating the pathologic condition because IFN-γ production is significantly suppressed unlike with α-galactosylceramide. Because compound (1) and the like have a sulfonamide group and hence exhibit extremely high polarities, it is possible to easily form a complex with the CD1d protein in APC, and it is also possible to improve the stability of the complex. Furthermore, even with a smaller dose of administration than that of α-galactosylceramide, NKT cells can be potently activated to increase the amount of IL-4 produced.

During the onset of an autoimmune disease, the Th1/Th2 immune balance is biased to Th1; by administering compound (1) and the like, the Th1/Th2 immune balance can be corrected. Therefore, it is possible to prevent or treat diseases resulting from functional accentuation of Th1 cells. For compound (1) and the like, the α-form and the β-form can be used alone or in combination; however, from the viewpoint of pharmacological effect, the α-form is preferred.

Autoimmune diseases that can be treated with compound (1) and the like relating to the present invention include multiple sclerosis, articular rheumatism, psoriasis, Crohn's disease, leukoderma vulgaris, Behcet's disease, collagenosis, type I diabetes mellitus, uveitis, Sjoegren's syndrome, autoimmune cardiomyotitis, autoimmune liver disease, autoimmune gastritis, pemphigus, Guillain-Barre syndrome, HTLV-1-related myelopathy and the like in mammals (e.g., mice, cats, bovines, dogs, horses, goats, monkeys, humans). Diseases resulting from functional accentuation of Th1 cells include multiple sclerosis, articular rheumatism, psoriasis, type I diabetes mellitus, uveitis, Sjoegren's syndrome, fulminant hepatitis, graft rejection, infectious diseases due to intracellularly infecting pathogens and the like in mammals.

When compound (1) and the like relating to the present invention is administered to a human, it can be safely administered orally or parenterally, as is or after being blended with a pharmacologically acceptable carrier, excipient, diluent and the like, in the form of pharmaceutical compositions such as oral preparations (e.g., powders, granules, tablets, capsules), parenteral preparations (e.g., injections), and suppositories (e.g., rectal suppositories, vaginal suppositories). These preparations can be produced by conventionally known methods.

Injections include subcutaneous injections, intravenous injections, intramuscular injections, intraperitoneal injections, drip infusions and the like. An injection can be prepared as an aqueous injection by treating compound (1) and the like in the presence of a solubilizer (e.g., β-cyclodextrins), a dispersing agent (e.g., carboxymethylcellulose, sodium alginate), a preservative (e.g., methylparaben, propylparaben, benzyl alcohol, chlorobutanol), an isotonizing agent (e.g., sodium chloride, glycerol, sorbitol, glucose) and the like by a conventional method. An injection can also be prepared as an oily injection by dissolving, suspending or emulsifying compound (1) and the like in a vegetable oil (e.g., olive oil, sesame oil, peanut oil, cottonseed oil, corn oil), propylene glycol and the like.

An oral preparation can also be produced by adding to compound (1) and the like, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethyleneglycol) and the like as appropriate, compression-molding the mixture, and then, as required, coating the mixture with hydroxypropylmethylcellulose and the like. A suppository can be produced by blending compound (1) and the like with a non-irritant excipient (e.g., polyethylene glycol, glycerides of higher fatty acids).

The dose of compound (1) and the like varies depending on the age, body weight, symptoms, dosage form, method of administration, duration of administration and the like; for example, for a patient (adult, weighing about 60 kg), a daily dose of 0.1 to 1 mg/kg, preferably 0.5 to 1 mg/kg, more preferably 0.8 to 1 mg/kg, is administered orally or parenterally in a single to several divided portions.

EXAMPLES

The present invention is explained in more detail in the following by referring to Examples, which are not to be construed as limitative.

Example 1

(2S,3S,4R)-1-(α-D-galactopyranosyloxy)-2-(p-toluenesulfonylamino)-3,4-octadecanediol (Compound 11)

(1) Synthesis of a Compound Represented by the Following Formula (B1)

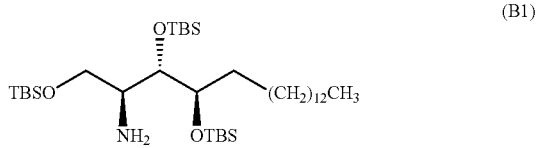

To a solution of commercially available phytosphingosine (6.81 g, 21.4 mmol, manufactured by Degussa Cosmoferm B.V.) in dichloromethane-2,6-lutidine (1:1, 500 mL) was added tert-butyldimethylsilyl trifluoromethanesulfonate (29.5 mL, 128 mmol) under ice-cooling. The mixture was stirred at room temperature for 24 hr, and the reaction was stopped by adding methanol (10 mL). After stirring for 1 hr, the mixture was concentrated under reduced pressure. The residue was purified by silica gel column chromatography (300 g, hexane-ethyl acetate=30:1) to give compound (B1) (11.4 g, 81%) as a colorless oil.

$n_D^{17}$=1.4604

$[\alpha]_D^{17}$=−2.69 (c=1.05, CHCl$_3$) IR (film): $\nu_{max}$=3400 (w, NH), 3320 (w, NH), 1255 (s, tBu, Si—CH$_3$), 1090 (br. s, C—O), 835 (s), 775 (s) cm$^{-1}$ $^1$H NMR (500 MHz, CDCl$_3$, 25° C.): δ=3.82 (dd, $^3J_{H,H}$=9.5, 3.5 Hz, 1H, 1-H$_b$), 3.83-3.79 (m, 1H, 4-H), 3.52 (dd, $^3J_{H,H}$=7.5, 1.5 Hz, 1H, 3-H), 3.44 (dd, $^3J_{H,H}$=9.5, 7.5 Hz, 1H, 1-H$_a$), 2.88 (dt, $^3J_{H,H}$=7.5, 3.5 Hz, 1H, 2-H), 1.60-1.34 (m, 4H, 5-H$_2$, NH$_2$), 1.34-1.23 (m, 24H, 17-, 16-, 15-, 14-, 13-, 12-, 11-, 10-, 9-, 8-, 7-, 6-H$_2$), 0.906 (s, 9H, tBu), 0.898 (s, 9H, tBu), 0.897 (s, 9H, tBu), 0.88 (t, $^3J_{H,H}$=7.0 Hz, 3H, 18-H$_3$), 0.09 (s, 6H, SiCH$_3$×2), 0.062 (s, 6H, SiCH$_3$×2), 0.055 (s, 3H, SiCH$_3$), 0.051 (s, 3H, SiCH$_3$) ppm $^{13}$C NMR (126 MHz, CDCl$_3$, 25° C.): δ=77.9, 76.4, 65.6, 55.4, 34.3, 31.9, 29.8, 29.70, 29.68, 29.67, 29.65, 29.63, 29.60, 29.4, 26.2, 26.1, 26.0, 25.9, 22.7, 18.25, 18.22, 18.20, 14.1, −3.6, −3.9, −4.7, −4.9, −5.28, −5.32 ppm (2) Synthesis of a Compound Represented by the Following Formula (C1)

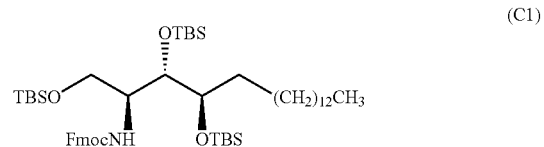

To a solution of compound (B1) (1.24 g, 1.88 mmol) in acetonitrile-tetrahydrofuran (1:1, 30 mL) was added 9-fluorenylmethyl succinimidyl carbonate (779 mg, 2.31 mmol) under ice-cooling. After stirring at room temperature for 16 hr, water was added and the mixture was extracted with diethyl ether. The organic layer was washed successively with water, saturated aqueous sodium hydrogen carbonate solution and saturated brine, and dried over anhydrous magnesium sulfate. After filtration, the solvent was evaporated by concentration under reduced pressure, and the residue was purified by silica gel column chromatography (25 g, hexane-ethyl acetate=30:1) to give compound (C1) (1.56 g, 94%) as a pale-yellow oil. In the formula, Fmoc means a 9-fluorenylmethoxycarbonyl group.

$n_D^{20}$=1.4968

$[\alpha]_D^{20}$=+7.08 (c=0.52, CHCl$_3$) IR (film): $\nu_{max}$=3445 (w, NH), 1735 (br. s, C=O), 1500 (m), 1250 (s, tBu, Si—CH$_3$), 1070 (br. m, C—O), 1060 (br. m, C—O), 835 (s), 780 (s), 740 (m) cm$^{-1}$ $^1$H NMR (500 MHz, CDCl$_3$, 25° C.): δ=7.76 (br. d, $^3J_{H,H}$=7.5 Hz, 2 H, Fmoc-aromat. H×2), 7.59 (br. d, $^3J_{H,H}$=7.5 Hz, 2H, Fmoc-aromat. H×2), 7.39 (br. t, $^3J_{H,H}$=7.5 Hz, 2H, Fmoc-aromat. H×2), 7.29 (br. tt, $^3J_{H,H}$=7.5, $^4J_{H,H}$=1.0 Hz, 2H, Fmoc-aromat. H×2), 5.18 (d, $^3J_{H,H}$=8.0 Hz, 1H, NH), 4.35 (d, $^3J_{H,H}$=7.0 Hz, 2H, Fmoc-1-H$_2$), 4.22 (br. t, $^3J_{H,H}$=7.0 Hz, 1H, Fmoc-9′-H), 3.86-3.81 (m, 2H, 3-H, 1-H$_a$), 3.77-3.69 (m, 3H, 4-, 2-H, 1-H$_a$), 1.57-1.46 (m, 2H, 5-H$_2$), 1.43-1.18 (m, 24H, 17-, 16-, 15-, 14-, 13-, 12-, 11-, 10-, 9-, 8-, 7-, 6-H$_2$), 0.91 (s, 9H, tBu), 0.901 (s, 9H, tBu), 0.897 (s, 9H, tBu), 0.88 (t, $^3J_{H,H}$=7.0 Hz, 3H, 18-H$_3$), 0.12 (s, 3H, SiCH$_3$), 0.07 (s, 3 H, SiCH$_3$), 0.06 (s, 9H, SiCH$_3$×3), 0.03 (s, 3H, SiCH$_3$) ppm $^{13}$C NMR (126 MHz, CDCl$_3$, 25° C.): δ=160.0, 144.1, 143.0, 141.3, 127.6, 127.0, 125.1, 119.9, 75.4, 75.2, 66.7, 61.5, 54.7, 47.2, 32.6, 31.9, 29.9, 29.70, 29.68, 29.66, 29.63, 29.61, 29.4, 26.1, 26.1, 25.8, 22.7, 18.33, 18.18, 18.16, 14.1, −3.7, −4.0, −4.7, −5.2, −5.3, −5.6 ppm (3) Synthesis of a Compound Represented by the Following Formula (D1)

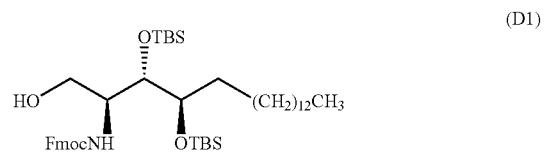

To a solution of compound (C1) (1.52 g, 1.72 mmol) in tetrahydrofuran (50 mL) was added 10% aqueous trifluoroacetic acid solution (10 mL) at −15° C. The mixture was allowed to warm to 20° C. by stirring for 4 hr. The reaction mixture was basified with 15% aqueous sodium hydroxide solution, diluted with diethyl ether, and the mixture was stirred at room temperature for 20 min. The organic layer was washed successively with water, saturated aqueous sodium hydrogen carbonate solution and saturated brine, and dried over anhydrous magnesium sulfate. After filtration, the solvent was evaporated by concentration under reduced pressure, and the residue was purified by silica gel column chromatography (50 g, hexane-ethyl acetate=10:1) to give compound (D1) (1.01 g, 76%) as a colorless oil.

$n_D^{20}$=1.5117

$[\alpha]_D^{20}$=−5.75 (c=0.59, CHCl$_3$) IR (film): $\nu_{max}$=3440 (m, NH), 3340 (s, O—H), 1710 (br. s, C=O), 1510 (s), 1255 (s, tBu, Si—CH$_3$), 1050 (br. s, C—O), 940 (m), 835 (s), 780 (s), 760 (m), 740 (m) cm$^{-1}$ $^1$H NMR (500 MHz, CDCl$_3$, 25° C.): δ=7.76 (br. d, $^3J_{H,H}$=7.5 Hz, 2 H, Fmoc-aromat. H×2), 7.60 (br. d, $^3J_{H,H}$=7.5 Hz, 1H, Fmoc-aromat. H), 7.59 (br. d, $^3J_{H,H}$=7.5 Hz, 1H, Fmoc-aromat. H), 7.40 (br. t, $^3J_{H,H}$=7.5 Hz, 1H, Fmoc-aromat. H), 7.39 (br. t, $^3J_{H,H}$=7.5 Hz, 1H, Fmoc-aromat. H), 7.30 (br. tt, $^3J_{H,H}$=7.5, $^4J_{H,H}$=1.0 Hz, 2H, Fmoc-aromat. H×2), 5.47 (d, $^3J_{H,H}$=8.5 Hz, 1H, NH), 4.44 (dd, $^3J_{H,H}$=10.5, 7.0 Hz, 1H, Fmoc-1-H$_a$), 4.38 (dd, $^3J_{H,H}$=10.5, 7.0 Hz, 1H, Fmoc-1-H$_b$), 4.21 (br. t, $^3J_{H,H}$=7.0 Hz, 1H, Fmoc-9'-H), 4.17 (dt, $^3J_{H,H}$=11.5, 3.5 Hz, 1H, 1-H$_a$), 3.92 (t, $^3J_{H,H}$=3.5 Hz, 1H, 3-H), 3.83 (dddd, $^3J_{H,H}$=8.5, 4.0, 3.5, 3.5 Hz, 1H, 2-H), 3.77 (dt, $^3J_{H,H}$=6.0, 3.5 Hz, 1H, 4-H), 3.66 (ddd, $^3J_{H,H}$=11.5, 9.0, 4.0 Hz, 1H, 1-H$_b$), 2.96 (dd, $^3J_{H,H}$=9.0, 3.5 Hz, 1H, OH), 1.59-1.48 (m, 2H, 5-H$_2$), 1.38-1.17 (m, 24H, 17-, 16-, 15-, 14-, 13-, 12-, 11-, 10-, 9-, 8-, 7-, 6-H$_2$), 0.912 (s, 9H, tBu), 0.905 (s, 9H, tBu), 0.88 (t, $^3J_{H,H}$=7.0 Hz, 3H, 18-H$_3$), 0.10 (s, 3H, SiCH$_3$), 0.09 (s, 3H, SiCH$_3$), 0.08 (s, 3H, SiCH$_3$), 0.04 (s, 3H, SiCH$_3$) ppm $^{13}$C NMR (126 MHz, CDCl$_3$, 25° C.): δ=155.9, 144.0, 143.8, 141.33, 141.30, 127.7, 127.02, 126.97, 125.1, 125.0, 120.0, 77.3, 75.9, 66.7, 63.3, 52.4, 47.2, 34.3, 31.9, 29.8, 29.68, 29.67, 29.66, 29.65, 29.61, 29.60, 29.5, 29.4, 26.0, 25.9, 25.6, 22.7, 18.16, 18.11, 14.1, −3.8, −4.2, −4.5, −5.1 ppm (4) Synthesis of a Compound Represented by the Following Formula (E1)

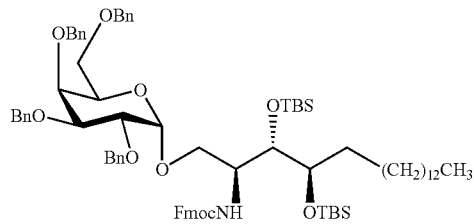

(E1)

To a solution of compound (D1) (931 mg, 1.21 mmol) in anhydrous tetrahydrofuran (40 mL) were successively added tin (II) chloride (684 mg, 3.61 mmol), silver perchlorate (750 mg, 3.61 mmol), and powdered molecular sieves (4A, 5.08 g), and the mixture was stirred at room temperature for 1 hr. The reaction mixture was cooled to −15° C., a solution of a compound represented by the following formula (J) (1.52 g, 2.72 mmol) in tetrahydrofuran (10 mL) was added, and the mixture was allowed to warm to 5° C. by stirring for 1 hr. The reaction mixture was diluted with diethyl ether, washed with saturated brine, and the organic layer was dried over anhydrous potassium carbonate. After filtration, the solvent was evaporated by concentration under reduced pressure, and the residue was purified by silica gel column chromatography (50 g, hexane-ethyl acetate=20:1) to give compound (E1) (742 mg, 61%) as a colorless oil.

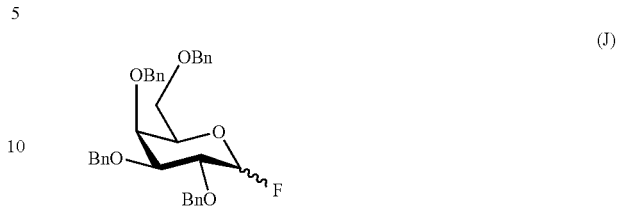

(J)

$n_D^{21}$=1.5170

$[\alpha]_D^{21}$=+13.9 (c=0.61, CHCl$_3$) IR (film): $\nu_{max}$=3340 (m, NH), 1730 (s, C=O), 1605 (w, aromat.), 1585 (w, aromat.), 1510 (w), 1500 (m, aromat.), 1250 (br. s, tBu, Si—CH$_3$), 1100 (br. s, C—O), 1055 (br. s, C—O), 835 (s), 780 (m) 740 (s), 695 (s) cm$^{-1}$ $^1$H NMR (500 MHz, CDCl$_3$, 25° C.): δ=7.71 (d, $^3J_{H,H}$=7.5 Hz, 2H, Fmoc-aromat. H×2), 7.57 (d, $^3J_{H,H}$=7.5 Hz, 1H, Fmoc-aromat. H), 7.51 (d, $^3J_{H,H}$=7.5 Hz, 1H, Fmoc-aromat. H), 7.36-7.19 (m, 24H, Bn-aromat. H×20, Fmoc-aromat. H×4), 5.51 (d, $^3J_{H,H}$=6.5 Hz, 1H, NH), 4.90 (d, $^3J_{H,H}$=11.5 Hz, 1H, Bn-H), 4.81 (d, $^3J_{H,H}$=4.0 Hz, 1H, 1'-H), 4.79 (d, $^3J_{H,H}$=12.0 Hz, 1H, Bn-H), 4.74 (d, $^3J_{H,H}$=12.0 Hz, 1H, Bn-H), 4.70 (d, $^3J_{H,H}$=12.0 Hz, 1 H, Bn-H), 4.65 (d, $^3J_{H,H}$=12.0 Hz, 1H, Bn-H), 4.54 (d, $^3J_{H,H}$=11.5 Hz, 1H, Bn-H), 4.42 (d, $^3J_{H,H}$=12.0 Hz, 1H, Bn-H), 4.36 (dd, $^3J_{H,H}$=10.5, 7.0 Hz, 1H, Fmoc-1-H$_a$), 4.33 (d, $^3J_{H,H}$=12.0 Hz, 1H, Bn-H), 4.31 (dd, $^3J_{H,H}$=10.5, 7.0 Hz, 1H, Fmoc-1-H$_b$), 4.15 (t, $^3J_{H,H}$=7.0 Hz, 1H, Fmoc-9'-H), 4.02 (dd, $^3J_{H,H}$=10.0, 3.5 Hz, 1H, 2'-H), 3.99-3.83 (m, 7H, 1-H$_2$, 2-, 3-, 3'-, 4'-, 5'-H), 3.69 (br. t, $^3J_{H,H}$=6.0 Hz, 4H), 3.48 (dd, $^3J_{H,H}$=9.0, 5.5 Hz, 1H, 6'-H$_a$), 3.45 (dd, $^3J_{H,H}$=9.0, 6.5 Hz, 1H, 6'-H$_b$), 1.51-1.46 (m, 2H, 5-H$_2$), 1.38-1.16 (m, 24H, 17-, 16-, 15-, 14-, 13-, 12-, 11-, 10-, 9-, 8-, 7-, 6-H$_2$), 0.90 (s, 9H, tBu), 0.88 (s, 9H, tBu), 0.88 (t, $^3J_{H,H}$=7.5 Hz, 3H, 18-H$_3$), 0.07 (s, 3H, SiCH$_3$), 0.05 (s, 3H, SiCH$_3$), 0.04 (s, 3H, SiCH$_3$), 0.02 (s, 3H, SiCH$_3$) ppm $^{13}$C NMR (126 MHz, CDCl$_3$, 25° C.): δ=156.1, 144.1, 143.9, 141.3, 141.2, 138.8, 138.7, 138.6, 137.8, 128.29, 128.27, 128.16, 127.8, 127.8, 127.6, 127.52, 127.48, 127.4, 127.3, 126.9, 125.1, 125.0, 119.9, 100.1, 79.1, 76.3, 75.48, 75.42, 74.9, 74.7, 73.4, 73.1, 73.0, 69.7, 69.4, 68.8, 66.4, 53.6, 47.2, 33.3, 31.9, 29.9, 29.69, 29.65, 29.63, 29.36, 26.13, 26.05, 25.9, 22.7, 18.3, 18.2, 14.1, −3.7, −4.0, −4.6, −5.0 ppm (5) Synthesis of a Compound Represented by the Following Formula (F1)

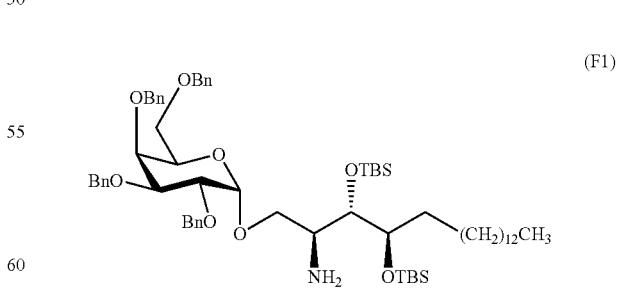

(F1)

To a solution of compound (E1) (2.61 g, 2.07 mmol) in N,N-dimethylformamide (100 mL) was added morpholine (100 mL), and the mixture was stirred at room temperature for 6 hr. The solvent was evaporated by concentration under reduced pressure, and the residue was diluted with ethyl acetate. This was successively washed with water and saturated brine, and dried over anhydrous potassium carbonate. After filtration, the solvent was evaporated by concentration under reduced pressure, and the residue was purified by silica gel column chromatography (20 g, hexane-ethyl acetate=50:4) to give compound (F1) (2.04 g, 92%) as a colorless oil.

$n_D^{23}$=1.5125

$[\alpha]_D^{23}$=+25.5 (c=1.01, CHCl$_3$) IR (film): $v_{max}$=3380 (w, NH), 3300 (w, NH), 1605 (w, aromat.), 1585 (w, aromat.), 1495 (m, aromat.), 1250 (s, tBu, Si—CH$_3$), 1100 (br. s, C—O), 1060 (br. s, C—O), 835 (s), 780 (s) 735 (s), 695 (s) cm$^{-1}$ $^1$H NMR (500 MHz, CDCl$_3$, 25° C.): δ=7.39-7.23 (m, 20H, Bn-aromat. H×20), 4.94 (d, $^3J_{H,H}$=11.5 Hz, 1H, Bn-H), 4.87 (d, $^3J_{H,H}$=4.0 Hz, 1H, 1'-H), 4.80 (d, $^3J_{H,H}$=12.0 Hz, 1H, Bn-H), 4.78 (d, $^3J_{H,H}$=12.0 Hz, 1H, Bn-H), 4.73 (d, $^3J_{H,H}$=12.0 Hz, 1 H, Bn-H), 4.67 (d, $^3J_{H,H}$=12.0 Hz, 1H, Bn-H), 4.56 (d, $^3J_{H,H}$=11.5 Hz, 1H, Bn-H), 4.43 (d, $^3J_{H,H}$=11.5 Hz, 1H, Bn-H), 4.38 (d, $^3J_{H,H}$=11.5 Hz, 1H, Bn-H), 4.05 (dd, $^3J_{H,H}$=10.0, 4.0 Hz, 1 H, 2'-H), 4.02-4.00 (m, 1H, 4'-H), 3.98 (dd, $^3J_{H,H}$=9.5, 3.0 Hz, 1H, 1-H$_a$), 3.98-3.94 (br. d, $^3J_{H,H}$=3.0 Hz, 1H, 5'-H), 3.94 (dd, $^3J_{H,H}$=10.0, 3.0 Hz, 3'-H), 3.74 (ddd, $^3J_{H,H}$=7.0, 5.0, 2.5 Hz, 1H, 4-H), 3.58 (t, $^3J_{H,H}$=9.0 Hz, 1H, 6'-H$_a$), 3.49 (dd, $^3J_{H,H}$=6.5, 2.5 Hz, 1H, 3-H), 3.46 (dd, $^3J_{H,H}$=9.0, 5.5 Hz, 1H, $^{6'}$-H$_b$), 3.20 (t, $^3J_{H,H}$=9.5 Hz, 1H, 1-H$_b$), 3.09 (ddd, $^3J_{H,H}$=9.5, 6.5, 3.0 Hz, 1H, 2-H), 1.52-1.43 (m, 2H, 5-H$_2$), 1.41-1.22 (m, 24H, 17-, 16-, 15-, 14-, 13-, 12-, 11-, 10-, 9-, 8-, 7-, 6-H$_2$), 0.888 (s, 9H, tBu), 0.879 (t, $^3J_{H,H}$=7.0 Hz, 3H, 18-H$_3$), 0.875 (s, 9H, tBu), 0.073 (s, 3H, SiCH$_3$), 0.070 (s, 3H, SiCH$_3$), 0.06 (s, 3H, SiCH$_3$), 0.05 (s, 3H, SiCH$_3$) ppm $^{13}$C NMR (126 MHz, CDCl$_3$, 25° C.): δ=138.79, 138.76, 138.6, 137.9, 128.36, 128.30, 128.28, 128.16, 128.10, 127.8, 127.75, 127.70, 127.51, 127.45, 127.39, 99.1, 79.0, 77.2, 76.7, 76.0, 74.79, 74.76, 73.5, 73.5, 72.8, 72.3, 69.2, 68.5, 53.6, 34.2, 31.9, 29.8, 29.69, 29.68, 29.65, 29.62, 29.4, 26.1, 25.9, 22.7, 18.23, 18.17, 14.1, −3.7, −3.9, −4.6, −4.7 ppm (6) Synthesis of a Compound Represented by the Following Formula (G1)

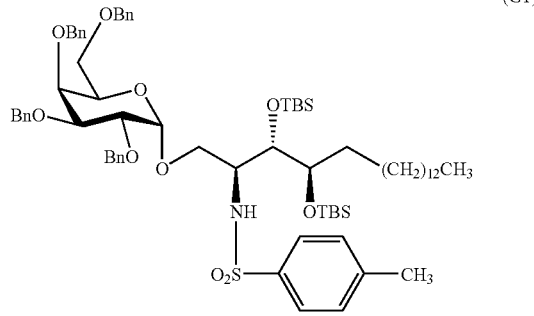

(G1)

To a solution of compound (F1) (150 mg, 0.140 mmol) and pyridine (1 mL) in chloroform (5 mL) were added p-toluenesulfonyl chloride (30 μL, 0.234 mmol) and N,N-dimethylaminopyridine (0.04 g) under ice-cooling. The mixture was stirred at room temperature for 23 hr, water was added and the mixture was further stirred for 1 hr. The mixture was extracted with diethyl ether, and the organic layer was washed successively with water, saturated aqueous copper sulfate solution, water, saturated aqueous sodium hydrogen carbonate solution and saturated brine, and dried over anhydrous magnesium sulfate. After filtration, the solvent was evaporated by concentration under reduced pressure, and the residue was purified by silica gel column chromatography (20 g, hexane-ethyl acetate=10:1) to give compound (G1) (123 mg, 73%) as a colorless oil.

$n_D^{25}$=1.5178

$[\alpha]_D^{25}$=−2.02 (c=0.88, CHCl$_3$) IR (film): $v_{max}$=3270 (m, NH), 1600 (m, aromat.), 1495 (s, aromat.), 1340 (m, SO$_2$), 1255 (s, tBu, Si—CH$_3$), 1165 (m, SO$_2$), 1090 (br. s, C—O), 1055 (br. s, C—O), 835 (s), 780 (s), 735 (m), 700 (s) cm$^{-1}$ $^1$H NMR (500 MHz, CDCl$_3$, 25° C.): δ=7.76 (d, $^3J_{H,H}$=8.0 Hz, 2H, aromat. H×2), 7.43-7.24 (m, 20H, Bn-aromat. H×20), 7.11 (d, $^3J_{H,H}$=8.0 Hz, 2H, aromat. H×2), 5.66 (d, $^3J_{H,H}$=4.0 Hz, 1H, NH), 4.91 (d, $^3J_{H,H}$=11.5 Hz, 1H, Bn-H), 4.88 (d, $^3J_{H,H}$=12.0 Hz, 1H, Bn-H), 4.80 (d, $^3J_{H,H}$=12.0 Hz, 1H, Bn-H), 4.76 (d, $^3J_{H,H}$=12.0 Hz, 1H, Bn-H), 4.67 (d, $^3J_{H,H}$=12.0 Hz, 1H, Bn-H), 4.55 (d, $^3J_{H,H}$=11.5 Hz, 1H, Bn-H), 4.49 (d, $^3J_{H,H}$=4.0 Hz, 1H, 1'-H), 4.43 (d, $^3J_{H,H}$=12.0 Hz, 1H, Bn-H), 4.40 (d, $^3J_{H,H}$=12.0 Hz, 1H, Bn-H), 4.10 (dd, $^3J_{H,H}$=4.0, 3.5 Hz, 1H, 3-H), 3.98 (dd, $^3J_{H,H}$=10.0, 4.0 Hz, 1H, 2'-H), 3.88 (br. d, $^3J_{H,H}$=3.0 Hz, 1H, 4'-H), 3.72-3.68 (m, 1H, 4-H), 3.70 (dd, $^3J_{H,H}$=10.0, 3.0 Hz, 1H, 3'-H), 3.67 (dd, $^3J_{H,H}$=11.0, 4.0 Hz, 1H, 1-H$_a$), 3.65 (br. t, $^3J_{H,H}$=7.0 Hz, 1H, 5'-H), 3.58 (dd, $^3J_{H,H}$=11.0, 8.0 Hz, 1H, 1-H$_b$), 3.41 (dd, $^3J_{H,H}$=9.0, 7.0 Hz, 1 H, 6'-H$_a$), 3.39 (dd, $^3J_{H,H}$=9.0, 6.0 Hz, 1H, 6'-H$_b$), 3.25 (dddd, $^3J_{H,H}$=8.0, 4.0, 4.0, 4.0 Hz, 1H, 2-H), 2.33 (s, 3H, CH$_3$), 1.45-1.23 (m, 26H, 17-, 16-, 15-, 14-, 13-, 12-, 11-, 10-, 9-, 8-, 7-, 6-, 5-H$_2$), 0.889 (s, 9H, tBu), 0.881 (t, $^3J_{H,H}$=7.0 Hz, 3H, 18-H$_3$), 0.80 (s, 9H, tBu), 0.18 (s, 3H, SiCH$_3$), 0.13 (s, 3H, SiCH$_3$), 0.02 (s, 3H, SiCH$_3$), −0.04 (s, 3 H, SiCH$_3$) ppm $^{13}$C NMR (126 MHz, CDCl$_3$, 25° C.): δ=142.9, 138.6, 138.5, 138.3, 137.7, 137.0, 129.5, 128.5, 128.4, 128.3, 128.22, 128.21, 128.14, 128.12, 127.77, 127.75, 127.62, 127.60, 127.2, 100.7, 79.3, 75.9, 75.2, 75.0, 74.7, 74.5, 73.7, 73.5, 72.7, 69.7, 68.7, 68.3, 55.2, 33.2, 31.9, 30.0, 29.70, 29.69, 29.65, 29.62, 29.4, 26.2, 25.9, 25.1, 22.7, 21.5, 18.4, 18.0, 14.1, −4.0, −4.17, −4.23, −4.6 ppm (7) Synthesis of a Compound Represented by the Following Formula (H1)

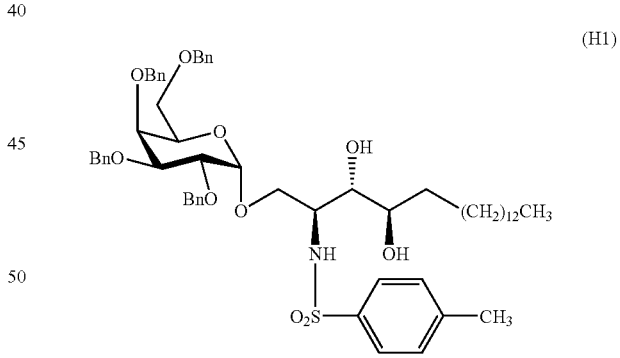

(H1)

To a solution of compound (G1) (94 mg, 0.077 mmol) in tetrahydrofuran (5 mL) was added tetrabutylammonium fluoride (1.0 M tetrahydrofuran solution, 308 μL, 0.308 mmol) at room temperature. The mixture was allowed to slowly warm to 60° C. with stirring, and the mixture was further stirred for 4 hr. Water was added, and the mixture was extracted with ethyl acetate. The organic layer was successively washed with water and saturated brine, and dried over anhydrous magnesium sulfate. After filtration, the solvent was evaporated by concentration under reduced pressure, and the residue was purified by silica gel column chromatography (10 g, hexane-ethyl acetate=4:1) to give compound (H1) (69 mg, 90%) as a colorless oil.

$n_D^{25}$=1.5179

$[\alpha]_D^{25}$=+44.7 (c=1.18, CHCl$_3$) IR (film): $\nu_{max}$=3480 (s, OH), 3280 (m, NH), 1600 (m, aromat.), 1495 (s, aromat.), 1330 (br. S, SO$_2$), 1165 (s, SO$_2$), 1095 (br. S, C—O), 1055 (br. s, C—O), 835 (s), 735 (br. s) 695 (s), 665 (m) cm$^{-1}$ $^1$H NMR (500 MHz, CDCl$_3$, 25° C.): δ=7.74 (d, $^3J_{H,H}$=8.5 Hz, 2H, aromat. H×2), 7.39-7.25 (m, 20H, Bn-aromat. H×20), 7.22 (d, $^3J_{H,H}$=8.5 Hz, 2H, aromat. H×2), 5.56 (d, $^3J_{H,H}$=8.5 Hz, 1H, NH), 4.89 (d, $^3J_{H,H}$=11.0 Hz, 1H, Bn-H), 4.86 (d, $^3J_{H,H}$=11.5 Hz, 1H, Bn-H), 4.76 (d, $^3J_{H,H}$=12.0 Hz, 1H, Bn-H), 4.74 (d, $^3J_{H,H}$=12.0 Hz, 1H, Bn-H), 4.72 (d, $^3J_{H,H}$=3.5 Hz, 1H, 1'-H), 4.63 (d, $^3J_{H,H}$=11.5 Hz, 1H, Bn-H), 4.55 (d, $^3J_{H,H}$=11.0 Hz, 1H, Bn-H), 4.52 (d, $^3J_{H,H}$=12.0 Hz, 1H, Bn-H), 4.42 (d, $^3J_{H,H}$=12.0 Hz, 1H, Bn-H), 4.00 (dd, $^3J_{H,H}$=10.0, 4.0 Hz, 1H, 2'-H), 3.98 (br. d, $^3J_{H,H}$=2.0 Hz, 1H, 4'-H), 3.86 (br. t, $^3J_{H,H}$=6.5 Hz, 1H, 5'-H), 3.84 (dd, $^3J_{H,H}$=10.0, 2.0 Hz, 1H, 3'-H), 3.82 (dd, $^3J_{H,H}$=10.5, 3.5 Hz, 1H, 1-H$_a$), 3.69 (dd, $^3J_{H,H}$=10.5, 3.0 Hz, 1H, 1-H$_b$), 3.55 (dddd, $^3J_{H,H}$=8.5, 3.5, 3.0, 3.0 Hz, 1H, 2-H), 3.50 (dd, $^3J_{H,H}$=9.0, 7.0 Hz, 1H, 6'-H$_a$), 3.47 (dd, $^3J_{H,H}$=9.0, 6.0 Hz, 1H, 6'-H$_b$), 3.40-3.35 (m, 1H, 4-H), 3.28 (br. d, $^3J_{H,H}$=10.0 Hz, 1H, OH), 3.21-3.16 (m, 1H, 3-H), 2.37 (s, 3H, CH$_3$), 1.93 (d, $^3J_{H,H}$=5.0 Hz, 1H, OH), 1.45-1.03 (m, 26H, 17-, 16-, 15-, 14-, 13-, 12-, 11-, 10-, 9-, 8-, 7-, 6-, 5-H$_2$), 0.88 (t, $^3J_{H,H}$=7.0 Hz, 3H, 18-H$_3$) ppm $^{13}$C NMR (126 MHz, CDCl$_3$, 25° C.): δ=143.3, 138.4, 138.3, 137.9, 137.8, 137.8, 129.7, 128.5, 128.4, 128.2, 128.14, 128.09, 128.0, 127.9, 127.8, 127.7, 127.6, 127.4, 127.0, 99.1, 79.5, 75.71, 75.66, 74.8, 74.32, 74.30, 73.5, 72.8, 72.6, 70.2, 69.7, 68.5, 53.0, 33.1, 31.9, 29.69, 29.68, 29.65, 29.63, 29.3, 25.5, 22.7, 21.5, 14.1 ppm (8) Synthesis of the Title Compound Represented by the Following Formula (11)

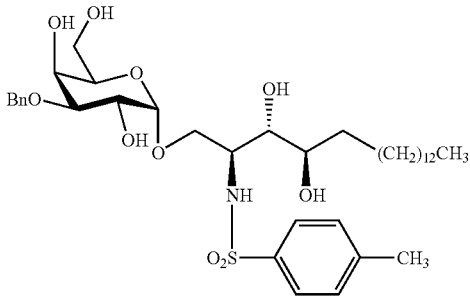

(11)

To a solution of compound (H1) (59 mg, 0.059 mmol) in ethanol-chloroform (4:1, 5 mL) was added palladium hydroxide (20%, 48 mg), and the mixture was stirred under a hydrogen atmosphere at room temperature for 16 hr. The palladium catalyst was removed by celite filtration, and the filtrate was concentrated under reduced pressure to evaporate the solvent. The residue was purified by silica gel column chromatography (20 g, chloroform-methanol=5:1) to give compound (11) (36 mg, 97%) as a colorless powder.

$[\alpha]_D^{26}$=+60.4 (c=0.72, pyridine) IR (KBr): $\nu_{max}$=3360 (br. s, OH, NH), 2920 (s, C—H), 2850 (s, C—H), 1650 (br. w), 1600 (w, aromat.), 1490 (w), 1465 (br. m), 1330 (br. m, SO$_2$), 1230 (w), 1160 (S, SO$_2$), 1070 (br. s, C—O), 1040 (m, C—O), 840 (w), 815 (m), 770 (w), 720 (w), 705 (w), 665 (s) cm$^{-1}$ $^1$H NMR (500 MHz, pyridine-d$_5$, 25° C.): δ=9.40 (d, $^3J_{H,H}$=8.5 Hz, 1H, NH), 8.15 (d, $^3J_{H,H}$=8.5 Hz, 2H, aromat. H×2), 7.17 (d, $^3J_{H,H}$=8.5 Hz, 2H, aromat. H×2), 6.78-6.62 (br. s, 6H, OH×6), 5.38 (d, $^3J_{H,H}$=3.5 Hz, 1H, 1'-H), 4.74-4.67 (m, 1H, 2-H), 4.67 (dd, $^3J_{H,H}$=10.5, 6.0 Hz, 1H, 1-H$_a$), 4.62 (dd, $^3J_{H,H}$=9.5, 3.5 Hz, 1H, 2'-H), 4.51 (d, $^3J_{H,H}$=3.5 Hz, 1H, 4'-H), 4.33 (dd, $^3J_{H,H}$=9.5, 3.5 Hz, 1H, 3'-H), 4.33-4.26 (m, 3H, 3-H, 6'-H$_2$), 4.26-4.20 (m, 2H, 4-, 5'-H), 4.20 (dd, $^3J_{H,H}$=10.5, 4.0 Hz, 1H, 1-H$_b$), 2.23-2.16 (m, 1H, 5-H$_a$), 2.14 (s. 3H, CH$_3$), 1.84-1.68 (m, 2H, 5-H$_b$, 6-H$_a$), 1.59-1.51 (m, 1H, 6-H$_b$), 1.39-1.16 (m, 22H, 17-, 16-, 15-, 14-, 13-, 12-, 11-, 10-, 9-, 8-, 7-H$_2$), 0.84 (t, $^3J_{H,H}$=7.5 Hz, 3H, 18-H$_3$) ppm $^{13}$C NMR (126 MHz, pyridine-d$_5$, 25° C.): δ=142.7, 140.5, 129.9, 127.4, 101.2, 77.3, 72.8, 72.3, 71.5, 70.9, 70.1, 67.8, 62.4, 55.3, 34.9, 32.1, 30.3, 30.1, 29.98, 29.96, 29.89, 29.6, 26.2, 22.9, 21.1, 14.3 ppm Example 2

(2S,3S,4R)-1-(α-D-galactopyranosyloxy)-2-(o-toluenesulfonylamino)-3,4-octadecanediol (Compound 12)

(1) Synthesis of a Compound Represented by the Following Formula (G2)

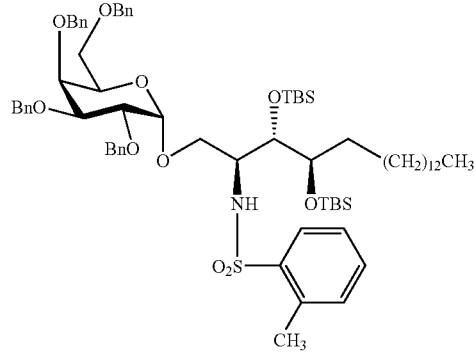

(G2)

In the same manner as in Example 1 except that o-toluenesulfonyl chloride instead of p-toluenesulfonyl chloride was used for compound (F1), compound (G2) was obtained as a colorless oil.

$n_D^{16}$=1.5185

$[\alpha]_D^{16}$=+1.72 (c=0.58, CHCl$_3$) IR (film): $\nu_{max}$=3280 (br. m, NH), 1600 (br. w, aromat.), 1495 (m, aromat.), 1335 (br. m, SO$_2$), 1250 (m, tBu, Si—CH$_3$), 1160 (m, SO$_2$), 1100 (br. s, C—O), 1055 (br. s, C—O), 835 (br. s), 780 (m), 695 (s) cm$^{-1}$ $^1$H NMR (500 MHz, CDCl$_3$, 25° C.): δ=7.97 (dd, $^3J_{H,H}$=8.0, $^4J_{H,H}$=1.5 Hz, 1H, aromat. H), 7.39-7.19 (m, 23H, aromat. H×3, Bn-aromat. H×20), 5.60 (d, $^3J_{H,H}$=5.0 Hz, 1H, NH), 4.90 (d, $^3J_{H,H}$=11.5 Hz, 1H, Bn-H), 4.80 (d, $^3J_{H,H}$=12.0 Hz, 1H, Bn-H), 4.77 (d, $^3J_{H,H}$=12.0 Hz, 1H, Bn-H), 4.72 (d, $^3J_{H,H}$=12.0 Hz, 1H, Bn-H), 4.64 (d, $^3J_{H,H}$=12.0 Hz, 1H, Bn-H), 4.63 (d, $^3J_{H,H}$=4.0 Hz, 1H, 1'-H), 4.54 (d, $^3J_{H,H}$=11.5 Hz, 1H, Bn-H), 4.45 (d, $^3J_{H,H}$=11.5 Hz, 1H, Bn-H), 4.40 (d, $^3J_{H,H}$=11.5 Hz, 1 H, Bn-H), 4.08 (dd, $^3J_{H,H}$=4.5, 3.0 Hz, 1H, 3-H), 4.00 (dd, $^3J_{H,H}$=10.0, 4.0 Hz, 1H, 2'-H), 3.91 (br. d, $^3J_{H,H}$=2.5 Hz, 1 H, 4'-H), 3.77 (dd, $^3J_{H,H}$=10.0, 2.5 Hz, 1H, 3'-H), 3.75 (br. t, $^3J_{H,H}$=6.5 Hz, 1H, 5'-H), 3.71-3.68 (m, 1H, 4-H), 3.68 (dd, $^3J_{H,H}$=11.0, 7.0 Hz, 1H, 1-H$_a$), 3.64 (dd, $^3J_{H,H}$=11.0, 4.5 Hz, 1H, 1-H$_b$), 3.43 (dd, $^3J_{H,H}$=8.5, 7.0 Hz, 1H, 6'-H$_a$), 3.41 (dd, $^3J_{H,H}$=8.5, 6.5 Hz, 1H, 6'-H$_b$), 3.31 (dddd, $^3J_{H,H}$=7.0, 5.0, 4.5, 4.5 Hz, 1H, 2-H), 2.62 (s, 3H, CH$_3$), 1.42-1.34 (m, 2H, 5-H$_2$), 1.34-1.17 (m, 24H, 17-, 16-, 15-, 14-, 13-, 12-, 11-, 10-, 9-, 8-, 7-, 6-H$_2$), 0.881 (t, $^3J_{H,H}$=7.0 Hz, 3H, 18-H$_3$), 0.880 (s, 9H, tBu), 0.80 (s, 9H, tBu), 0.16 (s, 3H, SiCH$_3$), 0.12 (s, 3H, SiCH$_3$), 0.05 (s, 3H, SiCH$_3$), −0.05 (s, 3 H, SiCH$_3$) ppm $^{13}$C NMR (126 MHz, CDCl$_3$, 25° C.): δ=138.60, 138.56, 138.4, 138.1, 137.7, 137.5, 132.47, 132.44, 129.6, 128.43, 128.37, 128.34, 128.2, 128.15, 128.08, 128.0, 127.74, 127.66, 127.58, 127.3, 126.1, 100.5, 79.1, 76.0, 75.2, 74.8, 74.7, 74.6, 73.6, 73.5, 72.8, 69.7, 68.6, 68.4, 55.2, 32.7, 31.9, 30.0, 29.71, 29.70, 29.66, 29.62, 29.4, 26.2, 26.0, 25.1, 22.7, 20.8, 18.4, 18.1, 14.1, −3.9, −4.2, −4.3, −4.6 ppm (2) Synthesis of a Compound Represented by the Following Formula (H2)

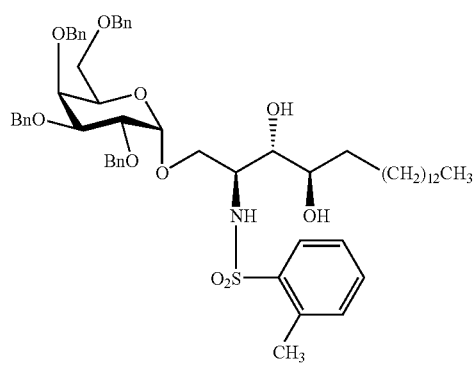

Compound (G2) was treated in the same manner as in Example 1 to give compound (H2) as a colorless oil.

$n_D^{26}$=1.5175

$[\alpha]_D^{26}$=+46.1 (c=0.50, CHCl$_3$) IR (film): $\nu_{max}$=3480 (br. s, OH), 3280 (br. m, NH), 1600 (br. w, aromat.), 1495 (m, aromat.), 1325 (br. m, SO$_2$), 1205 (w), 1160 (s, SO$_2$), 1100 (br. s, C—O), 1060 (br. s, C—O), 735 (br. s), 695 (s) cm$^{-1}$ $^1$H NMR (500 MHz, CDCl$_3$, 25° C.): δ=7.97 (dd, $^3J_{H,H}$=8.0, 1.5 Hz, 2H. aromat. H), 7.40-7.21 (m, 23H, aromat. H×3, Bn-aromat. H×20), 5.58 (d, $^3J_{H,H}$=9.0 Hz, 1H, NH), 4.89 (d, $^3J_{H,H}$=11.5 Hz, 1H, Bn-H), 4.87 (d, $^3J_{H,H}$=11.5 Hz, 1H, Bn-H), 4.77 (d, $^3J_{H,H}$=12.0 Hz, 1H, Bn-H), 4.74 (d, $^3J_{H,H}$=12.0 Hz, 1H, Bn-H), 4.73 (d, $^3J_{H,H}$=3.5 Hz, 1H, 1'-H), 4.64 (d, $^3J_{H,H}$=11.5 Hz, 1 H, Bn-H), 4.55 (d, $^3J_{H,H}$=11.5 Hz, 1H, Bn-H), 4.50 (d, $^3J_{H,H}$=11.5 Hz, 1H, Bn-H), 4.43 (d, $^3J_{H,H}$=11.5 Hz, 1H, Bn-H), 4.01-3.99 (m, 1H, 4'-H), 4.00 (dd, $^3J_{H,H}$=10.0, 3.5 Hz, 1H, 2'-H), 3.85 (dd, $^3J_{H,H}$=10.0, 2.5 Hz, 1H, 3'-H), 3.82 (br. t, $^3J_{H,H}$=6.5 Hz, 1H, 5'-H), 3.78 (dd, $^3J_{H,H}$=10.5, 2.5 Hz, 1H, 1-H$_a$), 3.66 (dd, $^3J_{H,H}$=10.5, 3.0 Hz, 1H, 1-H$_b$), 3.52-3.48 (m, 1H, 2-H), 3.50 (dd, $^3J_{H,H}$=9.0, 7.0 Hz, 1H, 6'-H$_a$), 3.44 (dd, $^3J_{H,H}$=9.0, 6.5 Hz, 1H, 6'-H$_b$), 3.39-3.33 (m, 1H, 4-H), 3.36 (d, $^3J_{H,H}$=10.0 Hz, 1H, OH), 3.21 (ddd, $J_{H,H}$=10.0, 6.5, 4.5 Hz, 1 H, 3-H), 2.64 (s, 3H, CH$_3$), 1.85 (d, $^3J_{H,H}$=5.5 Hz, 1H, OH), 1.42-1.00 (m, 26H, 17-, 16-, 15-, 14-, 13-, 12-, 11-, 10-, 9-, 8-, 7-, 6-, 5-H$_2$), 0.88 (t, $^3J_{H,H}$=7.0 Hz, 3H, 18-H$_3$) ppm $^{13}$C NMR (126 MHz, CDCl$_3$, 25° C.): δ=138.5, 138.4, 138.2, 137.8, 137.7, 137.0, 132.8, 132.5, 129.3, 128.47, 128.42, 128.2, 128.1, 128.0, 127.9, 127.8, 127.7, 127.6, 127.5, 126.2, 99.1, 79.4, 75.9, 75.6, 74.8, 74.4, 74.1, 73.5, 72.9, 72.5, 70.3, 69.7, 68.4, 52.8, 33.2, 31.9, 29.68, 29.67, 29.66, 29.64, 29.60, 29.57, 29.3, 25.5, 22.7, 20.2, 14.1 ppm (3) Synthesis of the Title Compound Represented by the Following Formula (12)

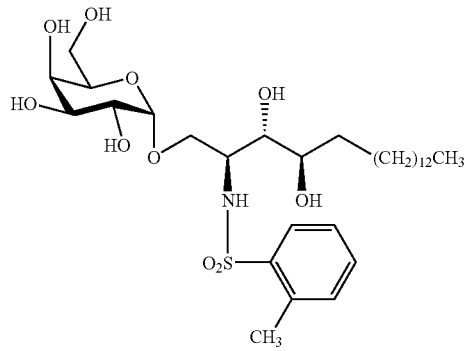

Compound (H2) was treated in the same manner as in Example 1 to give compound (12) as a colorless powder.

$[\alpha]_D^{24}$=+68.2 (c=0.35, pyridine) IR (KBr): $\nu_{max}$=3400 (br. s, OH, NH), 3060 (w), 2920 (s, C—H), 2850 (s, C—H), 1650 (br. w), 1595 (w, aromat.), 1465 (br. s), 1380 (w), 1325 (br. s, SO$_2$), 1225 (w), 1160 (S, SO$_2$), 1125 (w), 1070 (br. s, C—O), 1035 (br. s, C—O), 805 (w), 735 (m), 710 (m), 690 (w) cm$^{-1}$ $^1$H NMR (500 MHz, pyridine-d$_5$, 25° C.): δ=9.55 (br. d, $^3J_{H,H}$=8.5 Hz, 1H, NH), 8.40 (dd, $^3J_{H,H}$=8.0, $^4J_{H,H}$=1.5 Hz, 1H, aromat. H), 7.32 (dt, $^3J_{H,H}$=7.5, $^4J_{H,H}$=1.5 Hz, 1H, aromat. H), 7.26 (dd, $^3J_{H,H}$=7.5, $^4J_{H,H}$=0.5 Hz, 1H, aromat. H), 7.23 (ddd, $^3J_{H,H}$=8.0, 7.5, $^4J_{H,H}$=0.5 Hz, 1H, aromat. H), 7.01 (br. s, 1H, OH), 6.66 (br. s, 1H, OH), 6.60 (br. s, $^3J_{H,H}$=6.5 Hz, 1H, OH), 6.47 (br. t, $^3J_{H,H}$=5.5 Hz, 1H, OH), 6.33 (d, $^3J_{H,H}$=3.0 Hz, 1H, OH), 6.11 (br. d, $^3J_{H,H}$=5.0 Hz, 1H, OH), 5.34 (d, $^3J_{H,H}$=4.0 Hz, 1H, 1'-H), 4.63 (dd, $^3J_{H,H}$=10.0, 5.5 Hz, 1H, 1-H$_a$), 4.63-4.57 (m, 2H, 2-, 2'-H), 4.49 (br. s, 1H, 4'-H), 4.34-4.26 (m, 4H, 3-, 3'-H, 6'-H$_2$), 4.21 (dd, $^3J_{H,H}$=10.0, 4.0 Hz, 1H, 1-H$_b$), 4.22-4.17 (m, 2H, 4-, 5'-H), 2.89 (s, 3H, CH$_3$), 2.20-2.13 (m, 1H, 5-H$_a$), 1.83-1.75 (m, 1H, 6-H$_a$), 1.75-1.67 (m, 1H, 5-H$_b$), 1.56-1.47 (m, 1H, 6-H$_b$), 1.37-1.16 (m, 22H, 17-, 16-, 15-, 14-, 13-, 12-, 11-, 10-, 9-, 8-, 7-H$_2$), 0.84 (t, $^3J_{H,H}$=7.5 Hz, 3H, 18-H$_3$) ppm $^{13}$C NMR (126 MHz, pyridine-d$_5$, 25° C.): δ=141.0, 137.6, 132.8, 132.4, 129.6, 126.4, 101.4, 77.5, 72.8, 72.3, 71.5, 70.8, 70.1, 68.1, 62.4, 55.2, 34.8, 32.1, 30.3, 30.04, 29.95, 29.89, 29.6, 26.3, 22.9, 20.4, 14.3 ppm Example 3

(2S,3S,4R)-1-(α-D-galactopyranosyloxy)-2-(m-toluenesulfonylamino)-3,4-octadecanediol (Compound 13)

(1) Synthesis of a Compound Represented by the Following Formula (G3)

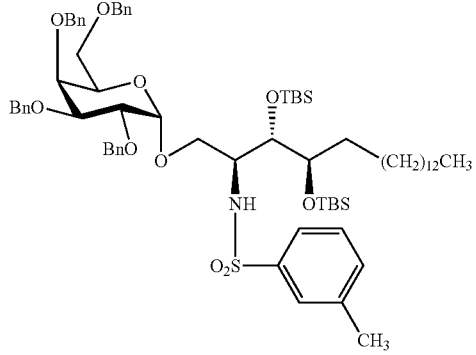

In the same manner as in Example 1 except that m-toluenesulfonyl chloride instead of p-toluenesulfonyl chloride was used for compound (F1), compound (G3) was obtained as a colorless oil.

$n_D^{13}$=1.5172

$[\alpha]_D^{16}$=+6.41 (c=0.65, CHCl$_3$) IR (film): $\nu_{max}$=3260 (br. m, NH), 1600 (w, aromat.), 1495 (m, aromat.), 1340 (m, SO$_2$), 1250 (s, tBu, Si—CH$_3$), 1160 (m, SO$_2$), 1100 (br. s, C—O), 1055 (br. s, C—O), 835 (s), 780 (s), 735 (br. m), 700 (s) cm$^{-1}$ $^1$H NMR (500 MHz, CDCl$_3$, 25° C.): δ=7.70 (d, $^3J_{H,H}$=7.5 Hz, 1H, aromat. H), 7.68 (s, 1H, aromat. H), 7.39 (br. d, $^3J_{H,H}$=7.5 Hz, 1H, aromat. H), 7.37-7.23 (m, 20H, Bn-aromat. H×20), 7.23 (t, $^3J_{H,H}$=7.5 Hz, 1H, aromat. H), 5.70 (d, $^3J_{H,H}$=5.0 Hz, 1H, NH), 4.90 (d, $^3J_{H,H}$=11.5 Hz, 1H, Bn-H), 4.86 (d, $^3J_{H,H}$=12.0 Hz, 1H, Bn-H), 4.78 (d, $^3J_{H,H}$=12.0 Hz, 1H, Bn-H), 4.73 (d, $^3J_{H,H}$=12.0 Hz, 1H, Bn-H), 4.66 (d, $^3J_{H,H}$=12.0 Hz, 1H, Bn-H), 4.54 (d, $^3J_{H,H}$=11.5 Hz, 1H, Bn-H), 4.50 (d, $^3J_{H,H}$=4.0 Hz, 1H, 1'-H), 4.45 (d, $^3J_{H,H}$=12.0 Hz, 1H, Bn-H), 4.41 (d, $^3J_{H,H}$=12.0 Hz, 1H, Bn-H), 4.01 (dd, $^3J_{H,H}$=4.5, 3.5 Hz, 1H, 3-H), 3.98 (dd, $^3J_{H,H}$=10.0, 4.0 Hz, 1H, 2'-H), 3.89 (d, $^3J_{H,H}$=2.5 Hz, 1H, 4'-H), 3.74-3.71 (m, 1H, 4-H), 3.73 (dd, $^3J_{H,H}$=10.0, 2.5 Hz, 1H, 3'-H), 3.70 (br. t, $^3J_{H,H}$=6.5 Hz, 1H, 5'-H), 3.65 (dd, $^3J_{H,H}$=11.0, 7.0 Hz, 1H, 1-H$_a$), 3.61 (dd, $^3J_{H,H}$=11.0, 4.5 Hz, 1H, 1-H$_b$), 3.41 (d, $^3J_{H,H}$=6.5 Hz, 2H, 6'-H$_2$), 3.29 (dddd, $^3J_{H,H}$=7.0, 5.0, 4.5, 4.5 Hz, 1H, 2-H), 2.35 (s, 3 H, CH$_3$), 1.45-1.23 (m, 26H, 17-, 16-, 15-, 14-, 13-, 12-, 11-, 10-, 9-, 8-, 7-, 6-, 5-H$_2$), 0.882 (s, 9H, tBu), 0.880 (t, $^3J_{H,H}$=7.0 Hz, 3H, 18-H$_3$), 0.81 (s, 9H, tBu), 0.16 (s, 3H, SiCH$_3$), 0.12 (s, 3H, SiCH$_3$), 0.02 (s, 3H, SiCH$_3$), −0.04 (s, 3 H, SiCH$_3$) ppm $^{13}$C NMR (126 MHz, CDCl$_3$, 25° C.): δ=140.0, 138.8, 138.55, 138.52, 138.3, 137.8, 133.1, 128.9, 128.46, 128.41, 128.34, 128.22, 128.15, 128.12, 128.10, 128.0, 127.74, 127.72, 127.6, 127.3, 124.5, 100.8, 79.3, 75.9, 75.3, 74.8, 74.7, 74.5, 73.7, 73.5, 72.8, 69.8, 68.8, 68.4, 55.3, 32.9, 31.9, 30.0, 29.70, 29.68, 29.67, 29.66, 29.64, 29.4, 26.2, 26.0, 25.2, 22.7, 21.4, 18.4, 18.1, 14.1, −4.0, −4.2, −4.3, −4.6 ppm (2) Synthesis of a Compound Represented by the Following Formula (H3)

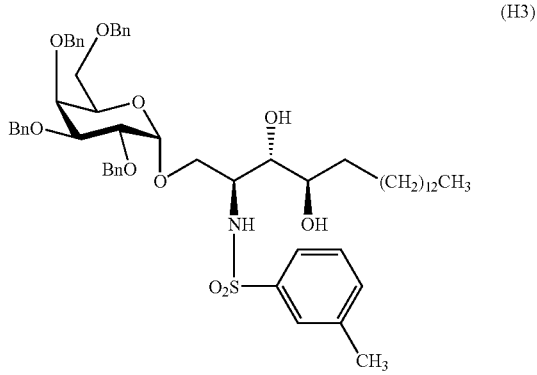

(H3)

Compound (G3) was treated in the same manner as in Example 1 to give compound (H3) as a colorless oil.

n$_D^{13}$=1.5179

[α]$_D^{14}$=+48.6 (c=0.55, CHCl$_3$) IR (film): ν$_{max}$=3480 (br. s, OH), 3240 (br. m, NH), 1600 (m, aromat.), 1590 (w, aromat.), 1495 (s, aromat.), 1330 (br. s, SO$_2$), 1155 (br. S, SO$_2$), 1090 (br. s, C—O), 1060 (br. s, C—O), 785 (m), 735 (br. s), 695 (s) cm$^{-1}$ $^1$H NMR (500 MHz, CDCl$_3$, 25° C.): δ=7.68 (br. s, 1H, aromat. H), 7.65 (br. t, $^3J_{H,H}$=3.5 Hz, 1H, aromat. H), 7.39-7.24 (m, 22 H, aromat. H×2, Bn-aromat. H×20), 5.57 (br. d, $^3J_{H,H}$=9.0 Hz, 1H, NH), 4.89 (d, $^3J_{H,H}$=12.0 Hz, 1H, Bn-H), 4.87 (d, $^3J_{H,H}$=12.0 Hz, 1H, Bn-H), 4.76 (d, $^3J_{H,H}$=11.5 Hz, 1H, Bn-H), 4.73 (d, $^3J_{H,H}$=11.5 Hz, 1H, Bn-H), 4.73 (d, $^3J_{H,H}$=4.0 Hz, 1 H, 1'-H), 4.63 (d, $^3J_{H,H}$=12.0 Hz, 1H, Bn-H), 4.55 (d, $^3J_{H,H}$=12.0 Hz, 1H, Bn-H), 4.51 (d, $^3J_{H,H}$=11.5 Hz, 1H, Bn-H), 4.42 (d, $^3J_{H,H}$=11.5 Hz, 1H, Bn-H), 4.00 (dd, $^3J_{H,H}$=10.0, 4.0 Hz, 1 H, 2'-H), 4.00-3.98 (m, 1H, 4'-H), 3.86 (br. t, $^3J_{H,H}$=6.5 Hz, 1H, 5'-H), 3.85 (dd, $^3J_{H,H}$=10.0, 2.5 Hz, 1H, 3'-H), 3.84 (dd, $^3J_{H,H}$=10.0, 3.0 Hz, 1H, 1-H$_a$), 3.70 (dd, $^3J_{H,H}$=10.0, 3.0 Hz, 1H, 1-H$_b$), 3.57 (dddd, $^3J_{H,H}$=9.0, 3.5, 3.0, 3.0 Hz, 1H, 2-H), 3.51 (dd, $^3J_{H,H}$=9.0, 7.0 Hz, 1H, 6'-H$_a$), 3.47 (dd, $^3J_{H,H}$=9.0, 6.0 Hz, 1H, 6'-H$_b$), 3.39-3.34 (m, 1H, 4-H), 3.32 (d, $^3J_{H,H}$=10.0 Hz, 1H, OH), 3.16 (ddd, $^3J_{H,H}$=10.0, 6.0, 3.5 Hz, 1H, 3-H), 2.37 (s, 3H, CH$_3$), 1.92 (d, $^3J_{H,H}$=5.0 Hz, 1H, OH), 1.42-1.03 (m, 26H, 17-, 16-, 15-, 14-, 13-, 12-, 11-, 10-, 9-, 8-, 7-, 6-, 5-H$_2$), 0.88 (t, $^3J_{H,H}$=7.0 Hz, 3H, 18-H$_3$) ppm $^{13}$C NMR (126 MHz, CDCl$_3$, 25° C.): δ=140.7, 139.3, 138.4, 138.2, 137.8, 137.7, 133.4, 129.0, 128.45, 128.42, 128.2, 128.12, 128.09, 127.98, 127.93, 127.75, 127.66, 127.63, 127.4, 127.3, 124.0, 99.1, 79.5, 75.72, 75.70, 74.8, 74.4, 74.3, 73.5, 72.8, 72.6, 70.4, 69.7, 68.4, 52.9, 33.1, 31.9, 29.68, 29.67, 29.65, 29.62, 29.3, 25.5, 22.7, 21.3, 14.1 ppm (3) Synthesis of the Title Compound Represented by the Following Formula (13)

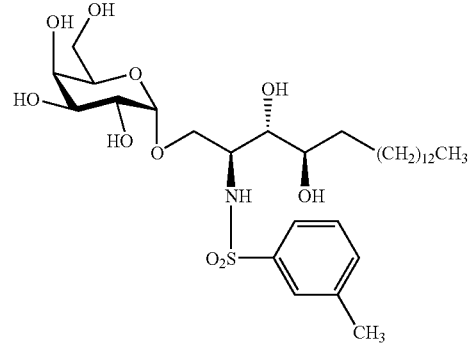

(13)

Compound (H3) was treated in the same manner as in Example 1 to give compound (13) as a colorless powder.

[α]$_D^{24}$=+75.4 (c=0.35, pyridine) IR (KBr): ν$_{max}$=3400 (br. s, OH, NH), 2920 (s, C—H), 2850 (s, C—H), 1600 (w, aromat.), 1465 (br. s), 1380 (w), 1330 (br. s, SO$_2$), 1305 (w), 1215 (m), 1155 (br. s, SO$_2$), 1125 (w), 1080 (br. s, C—O), 1035 (br. s, C—O), 930 (w), 890 (w), 785 (m), 720 (w), 690 (m) cm$^{-1}$ $^1$H NMR (500 MHz, pyridine-d$_5$, 25° C.): δ=9.44 (br. d, $^3J_{H,H}$=7.5 Hz, 1H, NH), 8.08 (dd, $^3J_{H,H}$=7.5, $^4J_{H,H}$=0.5 Hz, 1H, aromat. H), 8.06 (s, 1H, aromat. H), 7.30 (t, $^3J_{H,H}$=7.5, Hz, 1H, aromat. H), 7.19 (dd, $^3J_{H,H}$=7.5, $^4J_{H,H}$=0.5 Hz, 1H, aromat. H), 7.03 (br. s, 1H, OH), 6.72 (br. d, 1H, OH), 6.65 (br. s, $^3J_{H,H}$=6.5 Hz, 1H, OH), 6.42 (br. s, 1H, OH), 6.33 (br. d, 1 H, OH), 6.15 (br. d, $^3J_{H,H}$=4.0 Hz, 1H, OH), 5.35 (d, $^3J_{H,H}$=3.5 Hz, 1H, 1'-H), 4.75-4.71 (m, 1H, 2-H), 4.69 (dd, $^3J_{H,H}$=10.5, 6.0 Hz, 1H, 1-H$_a$), 4.61-4.57 (m, 1H, 2'-H), 4.50 (br. s, 1H, 4'-H), 4.35-4.27 (m, 4H, 3-, 3'-H, 6'-H$_2$), 4.25-4.20 (m, 2H, 4-, 5'-H), 4.17 (dd, $^3J_{H,H}$=10.5, 4.5 Hz, 1H, 1-H$_b$), 2.23-2.16 (m, 1H, 5-H$_a$), 2.15 (s, 3H, CH$_3$), 1.84-1.69 (m, 2 H, 5-H$_b$, 6-H$_a$), 1.59-1.51 (m, 1H, 6-H$_b$), 1.38-1.13 (m, 22H, 17-, 16-, 15-, 14-, 13-, 12-, 11-, 10-, 9-, 8-, 7-H$_2$), 0.84 (t, $^3J_{H,H}$=7.0 Hz, 3H, 18-H$_3$) ppm $^{13}$C NMR (126 MHz, pyridine-d$_5$, 25° C.): δ=143.2, 139.4, 133.0, 129.2, 127.8, 124.5, 101.3, 77.3, 72.9, 72.2, 71.5, 70.8, 70.2, 67.8, 62.4, 55.3, 34.9, 32.1, 30.3, 30.1, 29.97, 29.96, 29.89, 29.6, 26.2, 22.9, 21.0, 14.3 ppm Reference Example (2S,3S,4R)-1-(α-D-galactopyranosyloxy)-2-(hexadecanesulfonylamino)-3,4-octadecanediol (Compound 48)

(1) Synthesis of a Compound Represented by the Following Formula (P1)

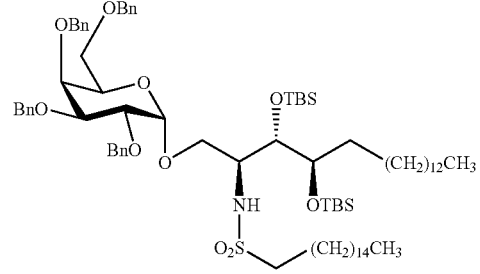

(P1)

In the same manner as in Example 1 except that hexadecanesulfonyl chloride instead of p-toluenesulfonyl chloride was used for compound (F1), compound (P1) was obtained as a colorless oil.

$n_D^{24}$=1.5060

$[\alpha]_D^{24}$=+13.4 (c=0.54, CHCl$_3$) IR (film): $\nu_{max}$=3280 (br. w, NH), 1610 (w, aromat.), 1495 (m, aromat.), 1330 (br. m, SO$_2$), 1255 (m, tBu, Si—CH$_3$), 1140 (br. s, SO$_2$), 1100 (br. s, C—O), 1060 (br. s, C—O), 835 (s), 780 (m), 735 (br. m), 695 (s) cm$^{-1}$ $^1$H NMR (500 MHz, CDCl$_3$, 25° C.): δ=7.37-7.24 (m, 20H, Bn-aromat. H×20), 4.91 (d, $^3J_{H,H}$=11.5 Hz, 1H, Bn-H), 4.87 (d, $^3J_{H,H}$=6.0 Hz, 1H, NH), 4.82 (d, $^3J_{H,H}$=12.0 Hz, 1H, Bn-H), 4.75 (d, $^3J_{H,H}$=12.0 Hz, 1H, Bn-H), 4.71 (d, $^3J_{H,H}$=4.0 Hz, 1 H, 1'-H), 4.70 (d, $^3J_{H,H}$=12.0 Hz, 1H, Bn-H), 4.64 (d, $^3J_{H,H}$=12.0 Hz, 1H, Bn-H), 4.55 (d, $^3J_{H,H}$=11.5 Hz, 1H, Bn-H), 4.45 (d, $^3J_{H,H}$=11.5 Hz, 1H, Bn-H), 4.40 (d, $^3J_{H,H}$=11.5 Hz, 1H, Bn-H), 4.04 (dd, $^3J_{H,H}$=10.0, 4.0 Hz, 1H, 2'-H), 4.00 (dd, $^3J_{H,H}$=10.5, 4.0 Hz, 1H, 1-H$_a$), 3.97 (br. d, $^3J_{H,H}$=2.5 Hz, 1 H, 4'-H), 3.92 (br. t, $^3J_{H,H}$=5.5 Hz, 1H, 5'-H), 3.91 (dd, $^3J_{H,H}$=8.0, 4.5 Hz, 1H, 3-H), 3.84 (dd, $^3J_{H,H}$=10.0, 3.0 Hz, 1H, 3'-H), 3.75 (dddd, $^3J_{H,H}$=8.0, 7.0, 6.0 Hz, 1H, 4-H), 3.65 (dddd, $^3J_{H,H}$=9.0, 6.0, 4.5, 4.0 Hz, 1H, 2-H), 3.50 (dd, $^3J_{H,H}$=10.5, 9.0 Hz, 1H, 1-H$_b$), 3.48 (dd, $^3J_{H,H}$=9.0, 5.5 Hz, 1H, 6'-H$_a$), 3.46 (dd, $^3J_{H,H}$=9.0, 5.5 Hz, 1H, 6'-H$_b$), 3.01 (dd, $^3J_{H,H}$=8.0, 7.5 Hz, 2H, 1''-H$_2$), 1.79-1.72 (m, 2H, 2'-H$_2$), 1.53-1.41 (m, 2H, 5-H$_2$), 1.38-1.17 (m, 50H, 17-, 16-, 15-, 14-, 13-, 12-, 11-, 10-, 9-, 8-, 7-, 6-, 15''-, 14''-, 13''-, 12''-, 11''-, 10''-, 9''-, 8''-, 7''-, 6''-, 5''-, 4''-, 3''-H$_2$), 0.89 (s, 9H, tBu), 0.880 (t, $^3J_{H,H}$=7.0 Hz, 6H, 18-, 16''-H$_3$), 0.880 (s, 9H, tBu), 0.14 (s, 3H, SiCH$_3$), 0.11 (s, 3 H, SiCH$_3$), 0.06 (s, 3H, SiCH$_3$), 0.05 (s, 3H, SiCH$_3$) ppm $^{13}$C NMR (126 MHz, CDCl$_3$, 25° C.): δ=138.56, 138.50, 138.3, 137.8, 128.45, 128.39, 128.35, 128.20, 128.12, 128.09, 127.9, 127.78, 127.73, 127.56, 127.54, 127.2, 100.1, 79.4, 76.4, 76.3, 74.9, 74.8, 74.7, 73.8, 73.5, 72.9, 69.8, 69.0, 68.5, 55.8, 52.9, 33.3, 31.9, 29.9, 29.70, 29.67, 29.64, 29.62, 29.59, 29.44, 29.36, 29.33, 28.6, 26.2, 26.0, 25.2, 23.4, 22.7, 18.3, 18.1, 14.1, −4.0, −4.2, −4.3, −4.4 ppm (2) Synthesis of a Compound Represented by the Following Formula (Q1)

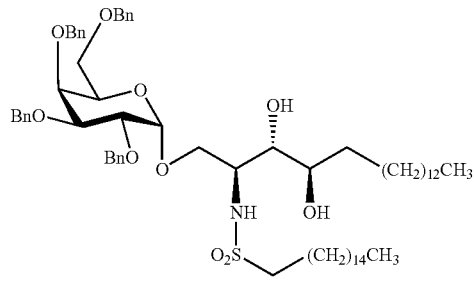

(Q1)

Compound (P1) was treated in the same manner as in Example 1 to give compound (Q1) as a colorless solid.

$[\alpha]_D^{26}$=+36.0 (c=0.34, CHCl$_3$) IR (KBr): $\nu_{max}$=3400 (br. s, OH), 3160 (br. m, NH), 1605 (w, aromat.), 1495 (m, aromat.), 1350 (m, SO$_2$), 1210 (m), 1100 (br. s, C—O), 1060 (br. s, C—O), 1035 (br. s, C—O), 750 (s), 730 (m), 695 (s) cm$^{-1}$ $^1$H NMR (500 MHz, CDCl$_3$, 25° C.): δ=7.38-7.25 (m, 20H, Bn-aromat. H×20), 5.18 (br. d, $^3J_{H,H}$=9.0 Hz, 1H, NH), 4.90 (d, $^3J_{H,H}$=11.5 Hz, 1H, Bn-H), 4.88 (d, $^3J_{H,H}$=11.5 Hz, 1H, Bn-H), 4.82 (d, $^3J_{H,H}$=4.0 Hz, 1H, 1'-H), 4.75 (s, 2H, Bn-H$_2$), 4.66 (d, $^3J_{H,H}$=11.5 Hz, 1H, Bn-H), 4.55 (d, $^3J_{H,H}$=11.5 Hz, 1H, Bn-H), 4.50 (d, $^3J_{H,H}$=12.0 Hz, 1H, Bn-H), 4.41 (d, $^3J_{H,H}$=12.0 Hz, 1H, Bn-H), 4.04 (dd, $^3J_{H,H}$=10.0, 4.0 Hz, 1H, 2'-H), 4.01 (dd, $^3J_{H,H}$=10.5, 2.5 Hz, 1H, 1-H$_a$), 3.99 (br. d, $^3J_{H,H}$=1.5 Hz, 1H, 4'-H), 3.94 (br. t, $^3J_{H,H}$=6.5 Hz, 1H, 5'-H), 3.87 (dd, $^3J_{H,H}$=10.0, 3.0 Hz, 1H, 3'-H), 3.78 (dd, $^3J_{H,H}$=10.5, 3.5 Hz, 1H, 1-H$_b$), 3.75 (dddd, $^3J_{H,H}$=9.0, 3.5, 3.0, 2.5 Hz, 1 H, 2-H), 3.52-3.45 (m, 2H, 3-, 4-H), 3.52 (dd, $^3J_{H,H}$=9.0, 6.0 Hz, 1H, 6'-H$_a$), 3.49 (dd, $^3J_{H,H}$=9.0, 7.0 Hz, 1H, 6'-H$_b$), 3.24 (d, $^3J_{H,H}$=9.5 Hz, 1H, OH), 3.01-2.97 (m, 2H, 1''-H$_2$), 2.07 (d, $^3J_{H,H}$=5.0 Hz, 1H, OH), 1.82-1.75 (m, 2H, 2''-H$_2$), 1.64-1.55 (m, 1H, 5-H$_a$), 1.48-1.39 (m, 1H, 5-H$_b$), 1.39-1.21 (m, 50 H, 17-, 16-, 15-, 14-, 13-, 12-, 11-, 10-, 9-, 8-, 7-, 6-, 15''-, 14''-, 13''-, 12''-, 11''-, 10''-, 9''-, 8''-, 7''-, 6''-, 5''-, 4''-, 3''-H$_2$), 0.88 (t, $^3J_{H,H}$=7.0 Hz, 6H, 18-, 16''-H$_3$) ppm $^{13}$C NMR (126 MHz, CDCl$_3$, 25° C.): 138.4, 138.2, 137.84, 137.79, 128.47, 128.45, 128.39, 128.24, 128.16, 128.07, 127.97, 127.8, 127.73, 127.65, 127.4, 98.9, 79.5, 76.87, 75.8, 74.8, 74.37, 74.3, 73.4, 73.0, 72.7, 70.4, 69.9, 68.7, 54.1, 53.4, 33.6, 31.9, 29.70, 29.65, 29.56, 29.4, 29.2, 28.3, 25.7, 23.7, 22.7, 14.1 ppm (3) Synthesis of the Title Compound Represented by the Following Formula (48)

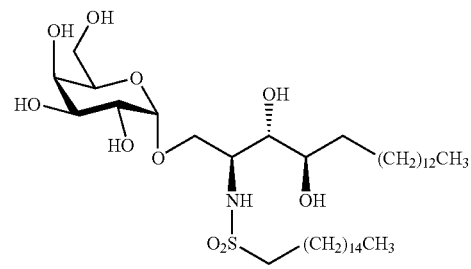

(48)

Compound (Q1) was treated in the same manner as in Example 1 to give compound (48) as a colorless powder.

$[\alpha]_D^{14}$=+55.0 (c=0.32, pyridine) IR (KBr): $\nu_{max}$=3400 (br. s, OH, NH), 2960 (s, C—H), 2920 (s, C—H), 2850 (s, C—H), 1470 (s), 1410 (w), 1380 (w), 1320 (br. m, SO$_2$), 1230 (w), 1150 (br. s, SO$_2$), 1075 (br. s, C—O), 1040 (br. s, C—O), 945 (w), 900 (br. w), 830 (w), 800 (w), 770 (w), 720 (m) cm$^{-1}$ $^1$H NMR (500 MHz, pyridine-d$_5$, 25° C.): δ=8.89 (d, $^3J_{H,H}$=9.5 Hz, 1H, NH), 6.81 (br. s, 1H, OH), 6.44-6.03 (br. s, 2H, OH×2), 5.52 (d, $^3J_{H,H}$=4.0 Hz, 1H, 1'-H), 5.36-4.75 (br. s, 3H, OH×3), 4.88 (dd, $^3J_{H,H}$=10.5, 5.0 Hz, 1H, 1-H$_a$), 4.88-4.83 (m, 1H, 2-H), 4.66 (dd, $^3J_{H,H}$=10.0, 4.0 Hz, 1H, 2'-H), 4.52 (br. d, $^3J_{H,H}$=3.5 Hz, 1H, 4'-H), 4.49 (br. t, $^3J_{H,H}$=6.0 Hz, 1H, 5'-H), 4.43 (dd, $^3J_{H,H}$=10.0, 3.5 Hz, 1H, 3'-H), 4.41 (dd, $^3J_{H,H}$=11.0, 6.0 Hz, 1H, 6'-H$_a$), 4.38-4.33 (m, 1H, 3-H), 4.36 (dd, $^3J_{H,H}$=11.0, 5.5 Hz, 1H, 6'-H$_b$), 4.33-4.27 (m, 2H, 1-H$_b$, 4-H), 3.51 (ddd, $^3J_{H,H}$=9.0, 6.5, 3.5 Hz, 2H, 1''-H$_2$), 2.36-2.28 (m, 1H, 5-H$_a$), 2.10-2.01 (m, 2H, 2''-H$_2$), 1.94-1.79 (m, 2H, 5-H$_b$, 6-H$_a$), 1.69-1.61 (m, 1H, 6-H$_b$), 1.45-1.14 (m, 48H, 17-, 16-, 15-, 14-, 13-, 12-, 11-, 10-, 9-, 8-, 7-, 15''-, 14''-, 13''-, 12''-, 11''-, 10''-, 9''-, 8''-, 7''-, 6''-, 5''-, 4''-, 3''-H$_2$), 0.84 (t, $^3J_{H,H}$=7.0 Hz, 6H, 18-, 16''-H$_3$) ppm $^{13}$C NMR (126 MHz, pyridine-d$_5$, 25° C.): δ=101.0, 78.3, 73.0, 72.4, 71.6, 71.0, 70.2, 68.3, 62.7, 55.9, 54.3, 35.1, 32.1, 29.98, 29.94, 29.92, 29.91, 29.89, 29.7, 29.6, 28.7, 26.4, 24.5, 22.9, 14.3 ppm Experimental Example 1

Splenocytes from a mouse spleen were prepared using an RPMI1640 culture broth (produced by Sigma) containing 10% Fetal calf serum (FCS) at 2×10$^5$ cells/well (96-well plate). A reagent was added to this culture broth at a concentration of 40 ng/mL; 3 days later (72 hours later), the cytokine content in the culture supernatant was measured by a sandwich ELISA technique. The test substances used were compound 11, compound 12 and compound 13 as obtained in Examples 1 to 3, with a compound represented by the following formula (a) (α-GalCer, hereinafter referred to as "compound a") used as the comparator.

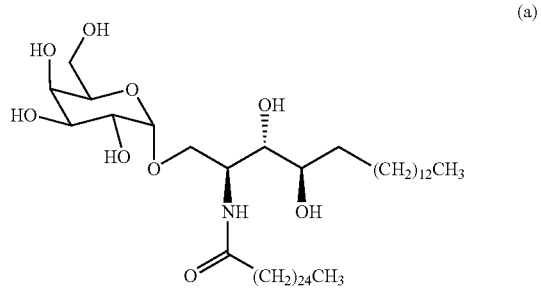

(a)

The results of measurements for IFN-γ and IL-4 are shown in FIG. 1. These results show that compound a produced both IFN-γ and IL-4 in large amounts, whereas compound 11, compound 12 and compound 13 exhibited an IL-4-predominant cytokine production pattern. These findings confirm that the compounds of the present invention are effective as therapeutic drugs for pathologic conditions that can be ameliorated by IL-4.

Experimental Example 2

Splenocytes taken out from a mouse spleen were prepared using an RPMI1640 culture broth (produced by Sigma) containing 10% Fetal calf serum (FCS) at $2\times10^5$ cells/well (96-well plate). A reagent was added to this culture broth at a concentration of 20 ng/mL; 2 days later (48 hours later), the cytokine content in the culture supernatant was measured by a sandwich ELISA technique. The test substances used were compound 11, compound 12, compound 13 and compound 48 as obtained in Examples 1 to 3 and Reference Example, with compound a and a compound represented by the following formula (b) (OCH, hereinafter referred to as compound b) used as the comparators.

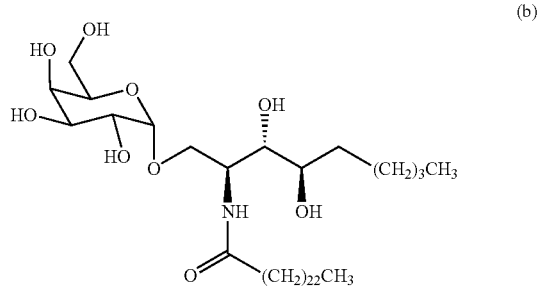

(b)

Figure 2:
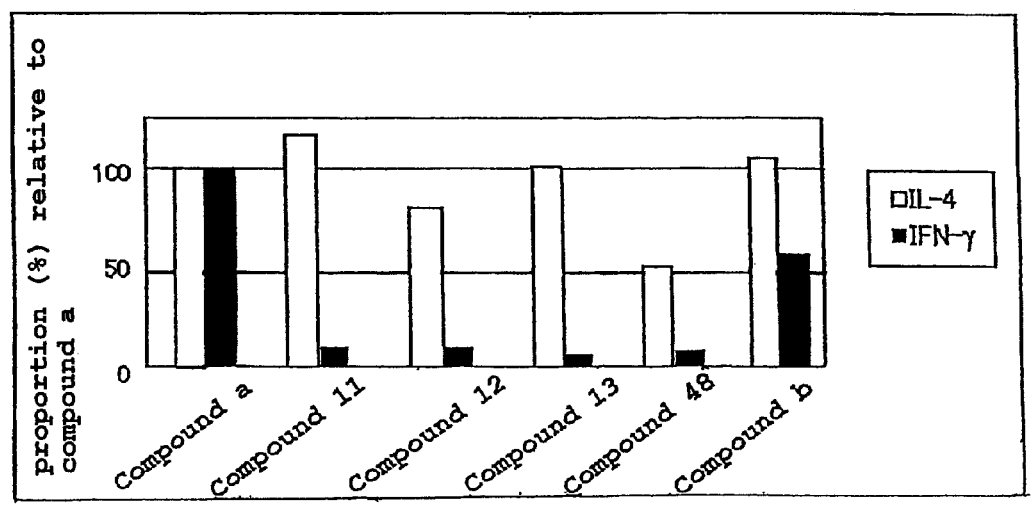
FIG. 2 shows the measurement results of IFN-γ production amount and IL-4 production amount in Experimental Example 2.

The results of measurements for IFN-γ and IL-4 are shown in FIG. 2. These results show that compound a produced both IFN-γ and IL-4 in large amounts, whereas compound 11, compound 12, compound 13 and compound 48 exhibited an IL-4-predominant cytokine production pattern with smaller amounts of IFN-γ produced. Compound b is known as a substance that induces IL-4-predominant cytokine production; it was confirmed that all of compound 11, compound 12, compound 13 and compound 48 as obtained in the Examples mentioned above are capable of inducing IL-4-predominant cytokine production to higher extents than compound b. These findings confirm that the compounds of the present invention are effective as therapeutic drugs for pathologic conditions that can be ameliorated by IL-4.

INDUSTRIAL APPLICABILITY

The novel glycolipid of the present invention is advantageous in that it can preferentially induce production of IL-4, which is one kind of cytokines that control action of immunocytes. Therefore, the novel glycolipid of the present invention is useful for the prophylaxis or treatment of autoimmune diseases, infectious diseases and the like, and prophylaxis or treatment of diseases caused by functional promotion of Th1 cells.

This application is based on a patent application No. 2006-054097 filed in Japan, the contents of which are incorporated in full herein by this reference.

The invention claimed is:

1. A compound represented by the following formula (1):

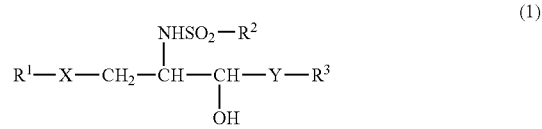

(1)

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —CH$_2$— or —NH—, and Y is —CH(OH)—, or a salt thereof.

2. The compound of claim 1, wherein $R^1$ is α-D-galactopyranosyl, or a salt thereof.

3. The compound of claim 1, wherein $R^2$ is an aromatic hydrocarbon group optionally having substituent(s) or a salt thereof.

4. The compound of claim 1, wherein $R^3$ is a $C_{1-21}$ alkyl group optionally having substituent(s), or a salt thereof.

5. The compound of claim 1, wherein X is an oxygen atom, or a salt thereof.

6. A compound represented by the following formula (2):

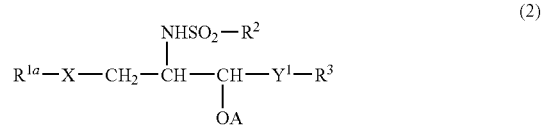

(2)

wherein $R^{1a}$ is an aldopyranose residue wherein the hydroxyl group is protected, $R^2$ is an aromatic group optionally having substituent(s), $R^3$ is a $C_{1-21}$ hydrocarbon group optionally having substituent(s), X is an oxygen atom, a sulfur atom, —CH$_2$— or —NH—, $Y^1$ is —CH(OA)-, and A is a hydrogen atom or a hydroxyl-protecting group, or a salt thereof.

7. A pharmaceutical agent comprising the compound represented by the following formula (1):

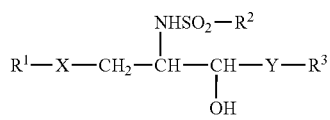
(1)

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —$CH_2$— or —NH—, Y is —CH(OH)—, or a salt thereof.

8. A method of treating an autoimmune disease or an infectious disease, which method comprises administering, to a subject, an effective amount of a compound represented by the following formula (1):

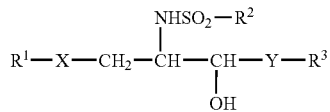
(1)

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —$CH_2$— or —NH—, Y is —$CH_2$—, —CH(OH)— or —CH=CH—, or a salt thereof, thereby treating an autoimmune disease or an infectious disease in the subject.

9. A method of activating NKT cell comprising contacting an NKT cell with a compound represented by the following formula (1):

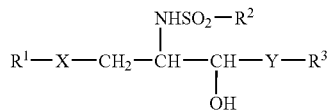
(1)

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —$CH_2$— or —NH—, Y is —$CH_2$—, —CH(OH)— or —CH=CH—, or a salt thereof, thereby activating the NKT cell.

10. A method of inducing selective IL-4 production comprising contacting an NKT cell with a compound represented by the following formula (1):

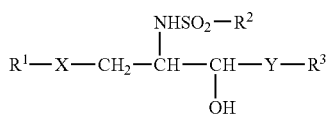
(1)

wherein $R^1$ is an aldopyranose residue, $R^2$ is an aromatic group optionally having substituent(s), $R^3$ is a $C_{1-21}$ hydrocarbon group optionally having substituent(s), X is an oxygen atom, a sulfur atom, —$CH_2$— or —NH—, Y is —CH(OH)—, or a salt thereof, thereby inducing selective IL-4 production.

11. A method of treating an autoimmune1 disease or an infectious disease, which method comprises administering, to a subject, an effective amount of a compound represented by the following formula (3):

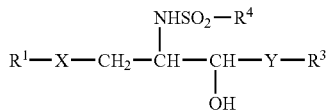
(3)

wherein $R^1$ is an aldopyranose residue, $R^3$ is a $C_{1-21}$ hydrocarbon group optionally having substituent(s), $R^4$ is a $C_{1-28}$ aliphatic hydrocarbon group optionally having substituent(s), X is an oxygen atom, and Y is —$CH_2$—, —CH(OH)— or —CH=CH—, or a salt thereof, thereby treating an autoimmune disease or an infectious disease in the subject.

12. A method of inducing selective IL-4 production comprising contacting an NKT cell with a compound represented by the following formula (3):

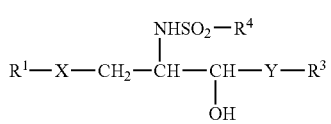
(3)

wherein $R^1$ is an aldopyranose residue, $R^3$ is a $C_{1-21}$ hydrocarbon group optionally having substituent(s), $R^4$ is a $C_{1-28}$ aliphatic hydrocarbon group optionally having substituent(s), X is an oxygen atom, and Y is —$CH_2$—, —CH(OH)— or —CH=CH—, or a salt thereof, thereby inducing selective IL-4 production.

* * * * *

UNITED STATES PATENT AND TRADEMARK OFFICE
CERTIFICATE OF CORRECTION

PATENT NO. : 8,163,705 B2
APPLICATION NO. : 12/281126
DATED : April 24, 2012
INVENTOR(S) : Tashiro et al.

It is certified that error appears in the above-identified patent and that said Letters Patent is hereby corrected as shown below:

*In the Claims*

Claim 11, column 42, line 17:

"autoimmune1 disease" should read "autoimmune disease"

Signed and Sealed this
Eighteenth Day of December, 2012

David J. Kappos
*Director of the United States Patent and Trademark Office*